US012385924B2

(12) United States Patent
Guo et al.

(10) Patent No.: US 12,385,924 B2
(45) Date of Patent: Aug. 12, 2025

(54) METHODS AND SYSTEMS FOR SENSITIVE AND MULTIPLEXED ANALYSIS OF BIOLOGICAL SAMPLES USING HIGH-PERFORMANCE CLEAVABLE, DETECTABLY-LABELED TYRAMIDE

(71) Applicants: Jia Guo, Tempe, AZ (US); Joshua LaBaer, Chandler, AZ (US)

(72) Inventors: Jia Guo, Tempe, AZ (US); Joshua LaBaer, Chandler, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 153 days.

(21) Appl. No.: 17/694,353

(22) Filed: Mar. 14, 2022

(65) Prior Publication Data

US 2022/0298562 A1 Sep. 22, 2022

Related U.S. Application Data

(60) Provisional application No. 63/162,290, filed on Mar. 17, 2021.

(51) Int. Cl.
*G01N 33/58* (2006.01)
*G01N 21/64* (2006.01)
*C12Q 1/6841* (2018.01)

(52) U.S. Cl.
CPC ....... *G01N 33/582* (2013.01); *G01N 21/6428* (2013.01); *C12Q 1/6841* (2013.01); *C12Q 2563/131* (2013.01); *G01N 2021/6441* (2013.01)

(58) Field of Classification Search
CPC .................................................. G01N 33/582
See application file for complete search history.

(56) References Cited

U.S. PATENT DOCUMENTS

| 6,066,459 A | 5/2000 | Garini et al. |
| 7,414,116 B2 | 8/2008 | Milton et al. |
| 8,753,828 B2 | 6/2014 | O'Keefe et al. |

FOREIGN PATENT DOCUMENTS

WO 2021171220 A1 9/2021

OTHER PUBLICATIONS

Abdelmohsen, K.; Gorospe, M. RNA-binding protein nucleolin in disease. RNA Biol. 2012, 9, 799-808, doi:10.4161/rna.19718.
Agard, N. J., Prescher, J. A. & Bertozzi, C. R. A Strain-Promoted [3+2] Azide-Alkyne Cycloaddition for Covalent Modification of Biomolecules in Living Systems. Journal of the American Chemical Society 126, 15046-15047 (2004).
Agrahari, A. K. et al. Cu(I)-Catalyzed Click Chemistry in Glycoscience and Their Diverse Applications. Chemical Reviews 121, 7638-7956 (2021).
Akama, K., Shirai, K. & Suzuki, S. Droplet-Free Digital Enzyme-Linked Immunosorbent Assay Based on a Tyramide Signal Amplification System. Anal. Chem. 88, 7123-7129 (2016).
Altelaar, a F.M.; Munoz, J.; Heck, A.J.R. Next-generation proteomics: towards an integrative view of proteome dynamics. Nat. Rev. Genet. 2012, 14, 35-48, doi:10.1038/nrg3356.
Amir, E. D. et al. viSNE enables visualization of high dimensional single-cell data and reveals phenotypic heterogeneity of leukemia. Nat. Biotechnol. 31, 545-52 (2013).
Angelo, M.; Bendall, S.C.; Finck, R.; Hale, M.B.; Hitzman, C.; Borowsky, A.D.; Levenson, R.M.; Lowe, J.B.; Liu, S.D.; Zhao, S.; et al. Multiplexed ion beam imaging of human breast tumors. Nat. Med. 2014, 20, 436-442, doi:10.1038/nm.3488.
Banerjee, A.; Apponi, L.H.; Pavlath, G.K.; Corbett, A.H. PABPN1: molecular function and muscle disease. FEBS J. 2013, 280, 4230-4250, doi:10.1111/febs.12294.
Baskin, J. M. & Bertozzi, C. R. Bioorthogonal Click Chemistry: Covalent Labeling in Living Systems. QSAR & Combinatorial Science 26, 1211-1219 (2007).
Bayani et al. (2004) Curr. Protocol. Cell Biol. 22.5.1-22.5.25.
Becskei, A.; Kaufmann, B.B.; van Oudenaarden, A. Contributions of low molecule number and chromosomal positioning to stochastic gene expression. Nat. Genet. 2005, 37, 937-944, doi:10.1038/ng1616.
Belkina, A. C. et al. Automated optimized parameters for T-distributed stochastic neighbor embedding improve visualization and analysis of large datasets. Nature Communications 10, 5415 (2019).
Bendall, S. C. et al. Single-cell mass cytometry of differential immune and drug responses across a human hematopoietic continuum. Science 332, 687-96 (2011).
Blackman, M. L., Royzen, M. & Fox, J. M. Tetrazine ligation: fast bioconjugation based on inverse-electron-demand Diels-Alder reactivity. Journal of the American Chemical Society 130, 13518-13519 (2008).
Blake, W.J.; KAErn, M.; Cantor, C.R.; Collins, J.J. Noise in eukaryotic gene expression. Nature 2003, 422, 633-637, doi:10.1038/nature01546.
Blow, N. Tissue preparation: Tissue issues. Nature 448, 959-960 (2007).
Box, J.K.; Paquet, N.; Adams, M.N.; Boucher, D.; Bolderson, E.; O'Byrne, K.J.; Richard, D.J. Nucleophosmin: from structure and function to disease development. BMC Mol. Biol. 2016, 17, 19, doi:10.1186/s12867-016-0073-9.
Castella, S.; Bernard, R.; Corno, M.; Fradin, A.; Larcher, J.-C. Ilf3 and NF90 functions in RNA biology. Wiley Interdiscip. Rev. RNA 2015, 6, 243-256, doi:10.1002/wrna.1270.
Chen, Q.; Xi, X.; Zeng, Y.; He, Z.; Zhao, J.; Li, Y. Acteoside inhibits autophagic apoptosis of retinal ganglion cells to rescue glaucoma-induced optic atrophy. J. Cell. Biochem. 2019, 120, 13133-13140, doi:10.1002/jcb.28586.

(Continued)

*Primary Examiner* — Shawquia Jackson
(74) *Attorney, Agent, or Firm* — Quarles & Brady, LLP

(57) ABSTRACT

Provided herein are methods for multiplexed in situ analysis of biomolecules in a tissue. In particular, provided herein are methods for multiplexed single-cell in situ protein and nucleic acid profiling in fixed or fresh tissues, that allows the investigation of the different cell compositions and their spatial organizations in intact tissues through consecutive cycles of probe hybridization, fluorescence imaging, and signal removal.

17 Claims, 16 Drawing Sheets
(16 of 16 Drawing Sheet(s) Filed in Color)

(56) References Cited

OTHER PUBLICATIONS

Chen, K. H.; Boettiger, a. N.; Moffitt, J. R.; Wang, S.; Zhuang, X. Science. 2015.

Cook, N. P., Kilpatrick, K., Segatori, L. & Martí, A. A. Detection of a-synuclein amyloidogenic aggregates in vitro and in cells using light-switching dipyridophenazine ruthenium(II) complexes. J. Am. Chem. Soc. 134, 20776-20782 (2012).

Coskun, A. F.; Cai, L. Nat. Methods 2016, 1.

Crosetto, N., Bienko, M. & Oudenaarden, A. Van. Spatially resolved transcriptomics and beyond. Nat. Rev. Genet. 16, 57-66 (2015).

Danilova et al. (2008) Chromosoma 117:345.

Darmanis, S. et al. A survey of human brain transcriptome diversity at the single cell level. Proc. Natl. Acad. Sci. U. S. A. 112, 7285-90 (2015).

Dore, K., Labrecque, S., Tardif, C. & De Koninck, P. Fret-Flim investigation of PSD95-NMDA receptor interaction in dendritic spines; control by calpain, CaMKII and Src family kinase. PLoS One 9, (2014).

Dubois, M.L.; Meller, A.; Samandi, S.; Brunelle, M.; Frion, J.; Brunet, M.A.; Toupin, A.; Beaudoin, M.C.; Jacques, J.F.; Lévesque, D.; et al. UBB pseudogene 4 encodes functional ubiquitin variants. Nat. Commun. 2020, 11, 1306. doi:10.1038/s41467-020-15090-6.

Duose, D.Y.; Schweller, R.M.; Zimak, J.; Rogers, A.R.; Hittelman, W.N.; Diehl, M.R. Configuring robust DNA strand displacement reactions for in situ molecular analyses. Nucleic Acids Res. 2012, 40, 3289-3298, doi:10.1093/nar/gkr1209.

Eisen, Michael B., Spellman, Paul T., Brown, Patrick O., Botstein, D. Cluster analysis and display of genome-wide expression patterns. Proc. Natl. Acad. Sci. USA 1998, 95, 14863-14868.

Elowitz, M.B.; Levine, A.J.; Siggia, E.D.; Swain, P.S. Stochastic gene expression in a single cell. Science 2002, 297, 1183-1186, doi:10.1126/science.1070919.

Eng, C.-H. L. et al. Transcriptome-scale super-resolved imaging in tissues by RNA seqFISH+. Nature 568, 235-239 (2019).

Espina, V. et al. Protein microarrays: Molecular profiling technologies for clinical specimens. Proteomics 3, 2091-2100 (2003).

Fan, R. et al. Integrated barcode chips for rapid, multiplexed analysis of proteins in microliter quantities of blood. Nat. Biotechnol. 26, 1373-8 (2008).

Fish Tag™ DNA Multicolor Kit instructions (Molecular probes) (2006).

Fransz et al. (2002) Proc. Natl. Acad. Sci. USA 99:14584.

Gerdes, M. J. et al. Highly multiplexed single-cell analysis of formalin-fixed, paraffin-embedded cancer tissue. Proc. Natl. Acad. Sci. U. S. A. 110, 11982-7 (2013).

Giesen, C.; Wang, H. a O.; Schapiro, D.; Zivanovic, N.; Jacobs, A.; Hattendorf, B.; Schüffler, P.J.; Grolimund, D.; Buhmann, J.M.; Brandt, S.; et al. Highly multiplexed imaging of tumor tissues with subcellular resolution by mass cytometry. Nat. Methods 2014, 11, 417-422, doi:10.1038/nmeth.2869.

Golding, I.; Paulsson, J.; Zawilski, S.M.; Cox, E.C. Real-time kinetics of gene activity in individual bacteria. Cell 2005, 123, 1025-1036, doi:10.1016/j.cell.2005.09.031.

Goltsev, Y.; Samusik, N.; Kennedy-Darling, J.; Bhate, S.; Hale, M.; Vazquez, G.; Black, S.; Nolan, G.P. Deep Profiling of Mouse Splenic Architecture with CODEX Multiplexed Imaging. Cell 2018, 174, 968-981.e15, doi:10.1016/j.cell.2018.07.010.

Guo, J.; Wang, S.; Dai, N.; Teo, Y.N.; Kool, E.T. Multispectral labeling of antibodies with polyfluorophores on a DNA backbone and application in cellular imaging. Proc. Natl. Acad. Sci. 2011, 108, 3493-3498, doi:10.1073/pnas.1017349108.

Gut, G.; Herrmann, M. D. & Pelkmans, L. Multiplexed protein maps link subcellular organization to cellular states. Science (80-. ). 361, eaar7042 (2018).

Harish, P.; Forrest, L.; Herath, S.; Dickson, G.; Malerba, A.; Popplewell, L. Inhibition of Myostatin Reduces Collagen Deposition in a Mouse Model of Oculopharyngeal Muscular Dystrophy (OPMD) With Established Disease. Front. Physiol. 2020, 11, 184. doi:10.3389/fphys.2020.00184.

Hausner, S. H., Marik, J., Gagnon, M. K. J. & Sutcliffe, J. L. In Vivo Positron Emission Tomography (PET) Imaging with an αvβ6 Specific Peptide Radiolabeled using 18F-"Click" Chemistry: Evaluation and Comparison with the Corresponding 4-[18F]Fluorobenzoyl- and 2-[18F]Fluoropropionyl-Peptides. Journal of Medicinal Chemistry 51, 5901-5904 (2008).

Jahan, S.; Sun, J.-M.; He, S.; Davie, J.R. Transcription-dependent association of HDAC2 with active chromatin. J. Cell. Physiol. 2018, 233, 1650-1657, doi:10.1002/jcp.26078.

Jean-Philippe, J.; Paz, S.; Caputi, M. hnRNP A1: the Swiss army knife of gene expression. Int. J. Mol. Sci. 2013, 14, 18999-19024, doi:10.3390/ijms140918999.

Jia, Q.; Nie, H.; Yu, P.; Xie, B.; Wang, C.; Yang, F.; Wei, G.; Ni, T. HNRNPA1-mediated 3' UTR length changes of HN1 contributes to cancer- and senescence-associated phenotypes. Aging (Albany. NY). 2019, 11, 4407-4437, doi:10.18632/aging.102060.

Jun, Y.W.; Kim, H.R.; Reo, Y.J.; Dai, M.; Ahn, K.H. Addressing the autofluorescence issue in deep tissue imaging by two-photon microscopy: The significance of far-red emitting dyes. Chem. Sci. 2017, 8, 7696-7704, doi:10.1039/c7sc03362a.

Junker, J.P.; Van Oudenaarden, A. Every cell is special: Genome-wide studies add a new dimension to single-cell biology. Cell 2014, 157, 8-11, doi:10.1016/j.cell.2014.02.010.

Kishi, J. Y. et al. SABER amplifies FISH: enhanced multiplexed imaging of RNA and DNA in cells and tissues. Nature Methods 16, 533-544 (2019).

Kleppe, M. et al. JAK-STAT pathway activation in malignant and nonmalignant cells contributes to MPN pathogenesis and therapeutic response. Cancer Discov. 5, 316-331 (2015).

Yeon, H., Cho, Y., Seo, J., Sim, Y. & Chang, J.-B. Simultaneous amplification of multiple immunofluorescence signals via cyclic staining of target molecules using mutually cross-adsorbed antibodies. Scientific Reports 12, 8780 (2022).

Zeng, D. et al. 64Cu Core-labeled nanoparticles with high specific activity via metal-free click chemistry. ACS nano 6, 5209-5219 (2012).

Zeng, D., Zeglis, B. M., Lewis, J. S. & Anderson, C. J. The growing impact of bioorthogonal click chemistry on the development of radiopharmaceuticals. Journal of Nuclear Medicine 54, 829-832 (2013).

Zhao, L.; Ke, H.; Xu, H.; Wang, G.D.; Zhang, H.; Zou, L.; Xiang, S.; Li, M.; Peng, L.; Zhou, M.; et al. TDP-43 facilitates milk lipid secretion by post-transcriptional regulation of Btn1a1 and Xdh. Nat. Commun. 2020, 11, 341. doi:10.1038/s41467-019-14183-1.

Zhao, P., Bhowmick, S., Yu, J. & Wang, J. Highly Multiplexed Single-Cell Protein Profiling with Large-Scale Convertible DNA-Antibody Barcoded Arrays. Adv. Sci. 1800672, 1800672 (2018).

Zrazhevskiy, P.; Gao, X. Quantum dot imaging platform for single-cell molecular profiling. Nat. Commun. 2013, 4, 1619, doi:10.1038/ncomms2635.

Klune, J. R.; Dhupar, R., Cardinal, J., Billiar, T. R. & Tsung, A. HMGB1: endogenous danger signaling. Mol. Med. 14, 476-84 (2008).

LaBaer, J.; Ramachandran, N. Protein microarrays as tools for functional proteomics. Curr. Opin. Chem. Biol. 2005, 9, 14-19. doi: 10.1016/j.cbpa.2004.12.006.

Lake, B. et al. Neuronal subtypes and diversity revealed by single-nucleus RNA sequencing of the human brain. Science (80-. ). 357, 352-357 (2016).

Lalmansingh, A.S.; Urekar, C.J.; Reddi, P.P. TDP-43 is a transcriptional repressor: the testis-specific mouse acrv1 gene is a TDP-43 target in vivo. J. Biol. Chem. 2011, 286, 10970-10982, doi:10.1074/jbc.M110.166587.

Lee, J. H.; Daugharthy, E. R.; Scheiman, J.; Kalhor, R.; Yang, J. L.; Ferrante, T. C.; Terry, R.; Jeanty, S. S. F.; Li, C.; A mamoto, R.; Peters, D. T.; Turczyk, B. M.; Marblestone, A. H.; Inverso, S. a; Bernard, A.; Mali, P.; Rios, X.; Aach, J.; Church, G. M. Science 2014, 343, 1360.

Lemieux, M. et al. Translocation of CaMKII to dendritic microtubules supports the plasticity of local synapses. J. Cell Biol. 198, 1055-1073 (2012).

Leriche et al., Bioorg. Med. Chem., 2012, 20:571-582.

(56) References Cited

OTHER PUBLICATIONS

Li, L.; Ghorbani, M.; Weisz-Hubshman, M.; Rousseau, J.; Thiffault, I.; Schnur, R.E.; Breen, C.; Oegema, R.; Weiss, M. M.M.; Waisfisz, Q.; et al. Lysine acetyltransferase 8 is involved in cerebral development and syndromic intellectual disability. J. Clin. Invest. 2020, 130, 1431-1445, doi:10.1172/JCI131145.

Liao, R.; Mondal, M.; Nazaroff, C.D.; Mastroeni, D.; Coleman, P.D.; Labaer, J.; Guo, J. Highly Sensitive and Multiplexed Protein Imaging With Cleavable Fluorescent Tyramide Reveals Human Neuronal Heterogeneity. Front. Cell Dev. Biol. 2021, 8, 1-15, doi:10.3389/fcell.2020.614624.

Liao, R.; Pham, T.; Mastroeni, D.; Coleman, P.D.; Labaer, J.; Guo, J. Highly Sensitive and Multiplexed In-Situ Protein Profiling with Cleavable Fluorescent Streptavidin. Cells 2020, 9, 852, doi:10.3390/cells9040852.

Lin, J.R.; Fallahi-Sichani, M.; Sorger, P.K. Highly multiplexed imaging of single cells using a high-throughput cyclic immunofluorescence method. Nat. Commun. 2015, 6, 1-7, doi:10.1038/ncomms9390.

Lin, Y.H.; Yao, M.C.; Wu, H.Y.; Dong, J.; Ni, H.Y.; Kou, X.L.; Chang, L.; Luo, C.X.; Zhu, D.Y. HDAC2 (Histone deacetylase 2): A critical factor in environmental enrichmentmediated stroke recovery. J. Neurochem. 2020, 155, 679-696. doi:10.1111/jnc.15043.

Lind, D., Franken, S., Kappler, J., Jankowski, J. & Schilling, K. Characterization of the neuronal marker NeuN as a multiply phosphorylated antigen with discrete subcellular localization. J. Neurosci. Res. 79, 295-302 (2005).

Liu, G.; Amin, S.; Okuhama, N.N.; Liao, G.; Mingle, L.A. A quantitative evaluation of peroxidase inhibitors for tyramide signal amplification mediated cytochemistry and histochemistry. Histochem. Cell Biol. 2006, 126, 283-291, doi:10.1007/s00418-006-0161-x.

Lu, J.; Gao, F.-H. Role and molecular mechanism of heterogeneous nuclear ribonucleoprotein K in tumor development and progression. Biomed. reports 2016, 4, 657-663, doi:10.3892/br.2016.642.

Lu, Y. et al. Highly multiplexed profiling of single-cell effector functions reveals deep functional heterogeneity in response to pathogenic ligands. Proc. Natl. Acad. Sci. U. S. A. 607-615 (2015). doi:10.1073/pnas.1416756112.

Martí, A. A., Jockusch, S., Stevens, N., Ju, J. & Turro, N. J. Fluorescent hybridization probes for sensitive and selective DNA and RNA detection. Acc. Chem. Res. 40, 402-409 (2007).

Maugeri, N.; Campana, L.; Gavina, M.; Covino, C.; De Metrio, M.; Panciroli, C.; Maiuri, L.; Maseri, A.; D'Angelo, A.; Bianchi, M.E.; et al. Activated platelets present high mobility group box 1 to neutrophils, inducing autophagy and promoting the extrusion of neutrophil extracellular traps. J. Thromb. Haemost. 2014, 12, 2074-2088, doi:10.1111/jth.12710.

Moffitt, J. R. et al. Molecular, spatial, and functional single-cell profiling of the hypothalamic preoptic region. Science 362, eaau5324 (2018).

Moffitt, J. R.; Hao, J.; Bambah-Mukku, D.; Lu, T.; Dulac, C.; Zhuang, X. Proc. Natl. Acad. Sci. 2016, 201617699, pp. 14456-14461.

Mondal, M., Liao, R. & Guo, J. Highly Multiplexed Single-Cell Protein Analysis. Chem.—A Eur. J. 1-10 (2018). doi:10.1002/chem.201705014.

Mondal, M.; Liao, R.; Nazaroff, C.D.; Samuel, A.D.; Guo, J. Highly multiplexed singlecell in situ RNA and DNA analysis with bioorthogonal cleavable fluorescent oligonucleotides. Chem. Sci. 2018, 9, 2909-2917, doi:10.1039/C7SC05089E.

Mondal, M.; Liao, R.; Xiao, L.; Eno, T.; Guo, J. Highly Multiplexed Single-Cell In Situ Protein Analysis with Cleavable Fluorescent Antibodies. Angew. Chemie Int. Ed. 2017, 56, 2636-2639, doi:10.1002/anie.201611641.

Munsky, B.; Neuert, G.; van Oudenaarden, a. Using Gene Expression Noise to Understand Gene Regulation. Science. 2012, 336, 183-187, doi:10.1126/science.1216379.

Ozbudak, E.M.; Thattai, M.; Kurtser, I.; Grossman, A.D.; van Oudenaarden, A. Regulation of noise in the expression of a single gene. Nat. Genet. 2002, 31, 69-73, doi:10.1038/ng869.

Pellegrini, L.; Hauser, D.N.; Li, Y.; Mamais, A.; Beilina, A.; Kumaran, R.; Wetzel, A.; Nixon-Abell, J.; Heaton, G.; Rudenko, I.; et al. Proteomic analysis reveals co-ordinated alterations in protein synthesis and degradation pathways in LRRK2 knockout mice. Hum. Mol. Genet. 2018, 27, 3257-3271, doi:10.1093/hmg/ddy232.

Pham, T., Liao, R., Labaer, J. & Guo, J. Multiplexed In Situ Protein Profiling with High-Performance Cleavable Fluorescent Tyramide. Molecules 26, (2021).

Piehowski, P. D. et al. Automated mass spectrometry imaging of over 2000 proteins from tissue sections at 100-µm spatial resolution. Nature Communications 11, 8 (2020).

Raj, A.; Peskin, C.S.; Tranchina, D.; Vargas, D.Y.; Tyagi, S. Stochastic mRNA synthesis in mammalian cells. PLoS Biol. 2006, 4, 1707-1719, doi:10.1371/journal.pbio.0040309.

Raser, J.M.; O'Shea, E.K. Control of stochasticity in eukaryotic gene expression. Science 2004, 304, 1811-1814, doi:10.1126/science.1098641.

Roberts et al. (1999) Genes Chrom. Cancer 25:241.

Robertson, D.; Savage, K.; Reis-Filho, J.S.; Isacke, C.M. Multiple immunofluorescence labeling of formalin-fixed paraffin-embedded tissue. BMC Mol. Biol. 2008, 9, 1-10, doi:10.1007/978-1-61779-055-3_4.

Rosenfeld, N.; Young, J.W.; Alon, U.; Swain, P.S.; Elowitz, M.B. Gene Regulation at the Single-Cell Level. Science 2005, 307, 1962-1965.

Saka, S.K.; Wang, Y.; Kishi, J.Y.; Zhu, A.; Zeng, Y.; Xie, W.; Kirli, K.; Yapp, C.; Cicconet, M.; Beliveau, B.J.; et al. Immuno-SABER enables highly multiplexed and amplified protein imaging in tissues. Nat. Biotechnol. 2019, 37, 1080-1090, doi:10.1038/s41587-019-0207-y.

Schrock et al. (1996) Science 273:494.

Schubert, W. et al. Analyzing proteome topology and function by automated multidimensional fluorescence microscopy. Nat. Biotechnol. 24, 1270-8 (2006).

Schweller, R.M.; Zimak, J.; Duose, D.Y.; Qutub, A. a; Hittelman, W.N.; Diehl, M.R. Multiplexed in situ immunofluorescence using dynamic DNA complexes. Angew. Chem. Int. Ed. Engl. 2012, 51, 9292-9296, doi:10.1002/anie.201204304.

Shah, S.; Lubeck, E.; Zhou, W.; Cai, L. Neuron 2016, 92, 342.

Stack, E.C.; Wang, C.; Roman, K.A.; Hoyt, C.C. Multiplexed immunohistochemistry, imaging, and quantitation: A review, with an assessment of Tyramide signal amplification, multispectral imaging and multiplex analysis. Methods 2014, 70, 46-58, doi:10.1016/j.ymeth.2014.08.016.

Steininger, R.J.; Rajaram, S.; Girard, L.; Minna, J.D.; Wu, L.F.; Altschuler, S.J. On comparing heterogeneity across biomarkers. Cytom. Part A 2015, 87, 558-567, doi:10.1002/cyto.a.22599.

Thul, P.J.; Akesson, L.; Wiking, M.; Mahdessian, D.; Geladaki, A.; Ait Blal, H.; Alm, T.; Asplund, A.; Björk, L.; Breckels, L.M.; et al. A subcellular map of the human proteome. Science. 2017, 356, doi:10.1126/science.aal3321.

Uhlén, M.; Fagerberg, L.; Hallström, B.M.; Lindskog, C.; Oksvold, P.; Mardinoglu, A.; Sivertsson, Å.; Kampf, C.; Sjöstedt, E.; Asplund, A.; et al. Tissue-based map of the human proteome. Science 2015, 347, 1260419, doi:10.1126/science.1260419.

Van de Corput, M.P.; Dirks, R.W.; van Gijlswijk, R.P.; van de Rijke, F.M.; Raap, A.K. Fluorescence in situ hybridization using horseradish peroxidase-labeled oligodeoxynucleotides and tyramide signal amplification for sensitive DNA and mRNA detection. Histochem. Cell Biol. 1998, 110, 431-437.

Wang, F. et al. RNAscope: A Novel in Situ RNA Analysis Platform for Formalin-Fixed, Paraffin-Embedded Tissues. The Journal of Molecular Diagnostics 14, 22-29 (2012).

Watson, S.F.; Bellora, N.; Maclas, S. ILF3 contributes to the establishment of the antiviral type i interferon program. Nucleic Acids Res. 2020, 48, 116-129, doi:10.1093/nar/gkz1060.

Wu, J., Zheng, G. & Lee, L. M. Optical imaging techniques in microfluidics and their applications. Lab Chip 12, 3566-3575 (2012).

Xiao JoshuaAU-Guo, JiaTI—Highly Sensitive and Multiplexed In Situ RNA Profiling with Cleavable Fluorescent Tyramide, L.-L. Highly Sensitive and Multiplexed In Situ RNA Profiling with Cleavable Fluorescent Tyramide. Cells 10, (2021).

(56) References Cited

OTHER PUBLICATIONS

Xiao RenjieAU-Guo, JiaTI—Highly Multiplexed Single-Cell In Situ RNA and DNA Analysis by Consecutive Hybridization, L.-L. Highly Multiplexed Single-Cell In Situ RNA and DNA Analysis by Consecutive Hybridization. Molecules 25, (2020).

Xie, R. et al. Factors influencing the degradation of archival formalin-fixed paraffin-embedded tissue sections. J. Histochem. Cytochem. 59, 356-65 (2011).

Xue, M.; Wei, W.; Su, Y.; Kim, J.; Shin, Y.S.; Mai, W.X.; Nathanson, D. a.; Heath, J.R. Chemical methods for the simultaneous quantitation of metabolites and proteins from single cells. J. Am. Chem. Soc. 2015, 137, 4066-4069, doi:10.1021/jacs.5b00944.

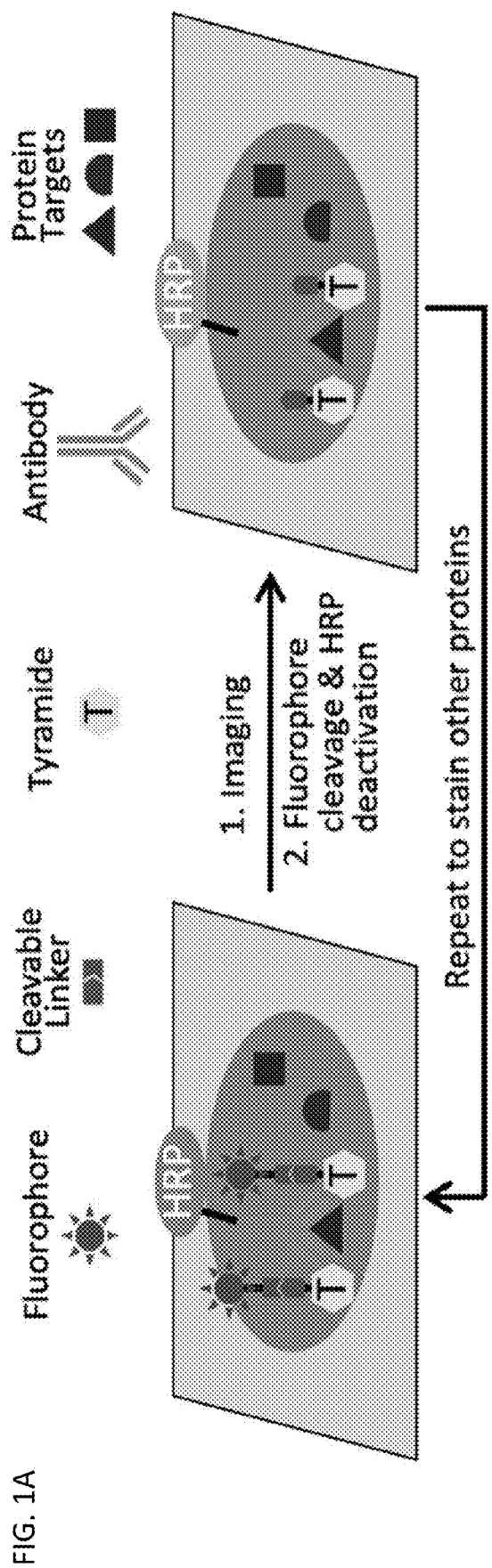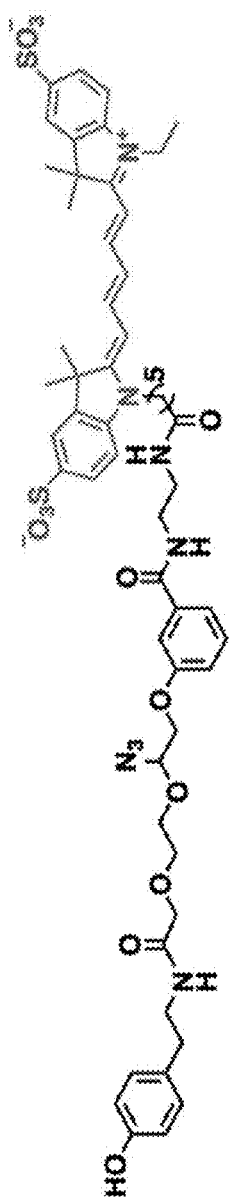
FIG. 1A
FIG. 1B

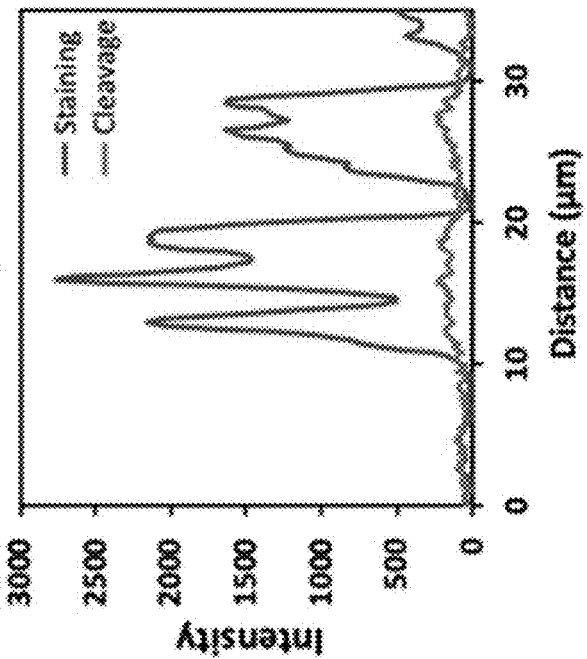
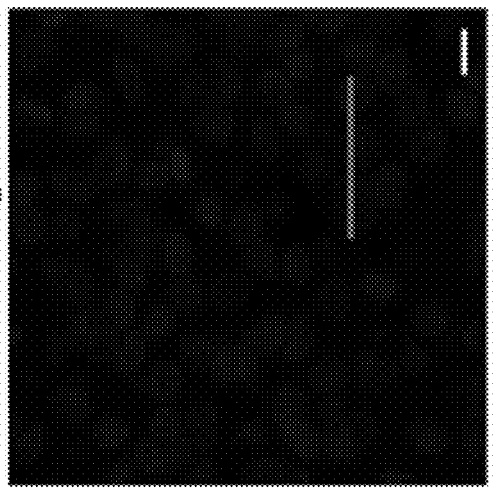
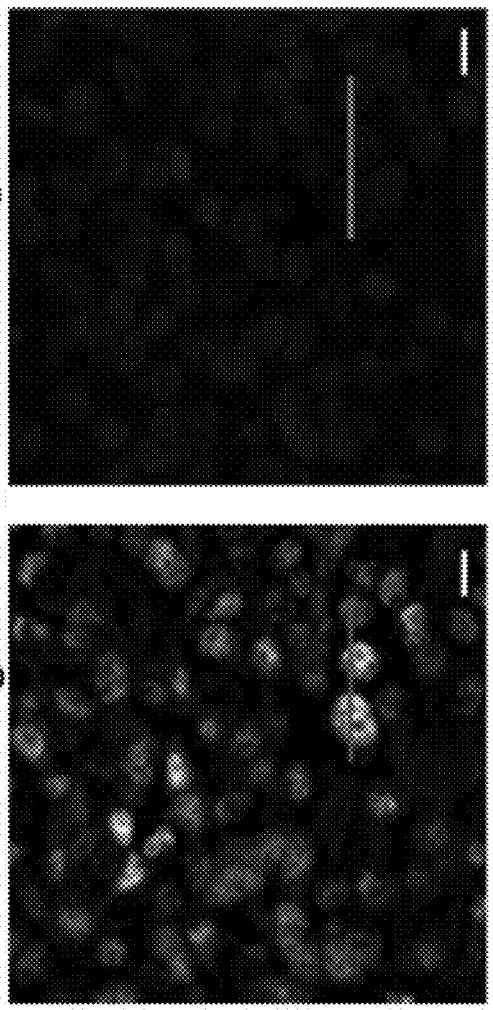

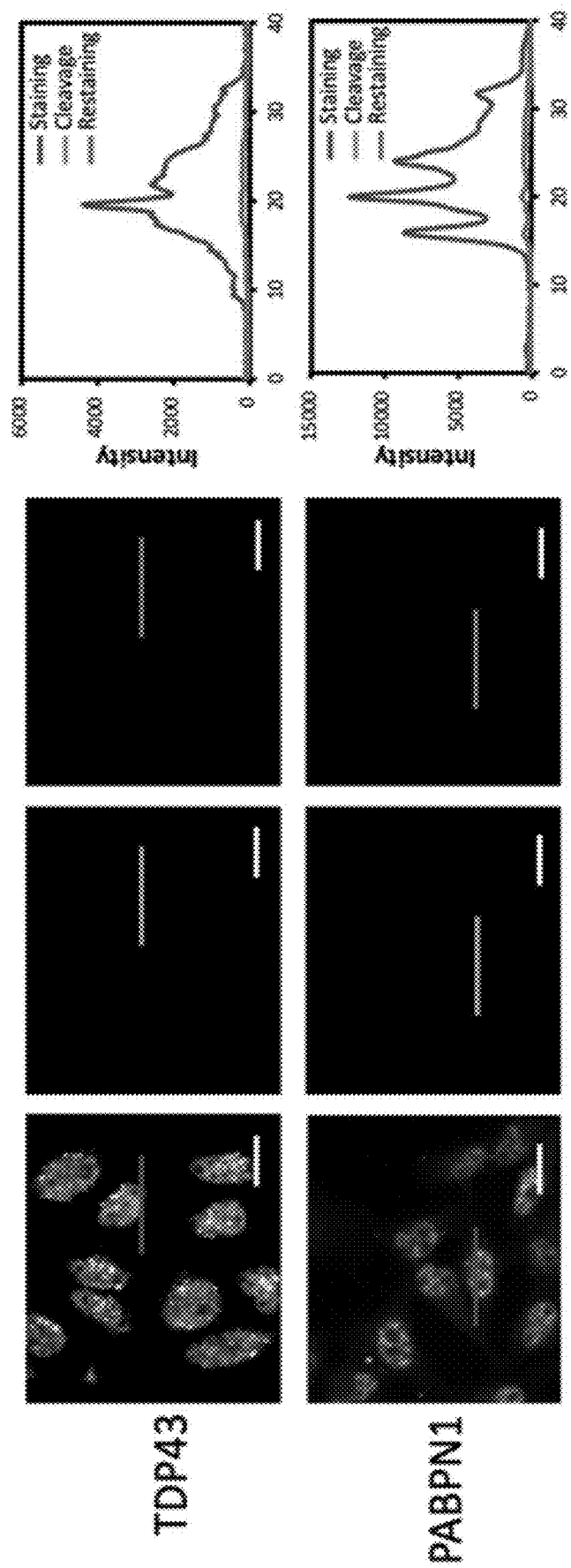
Figure 4, con't.

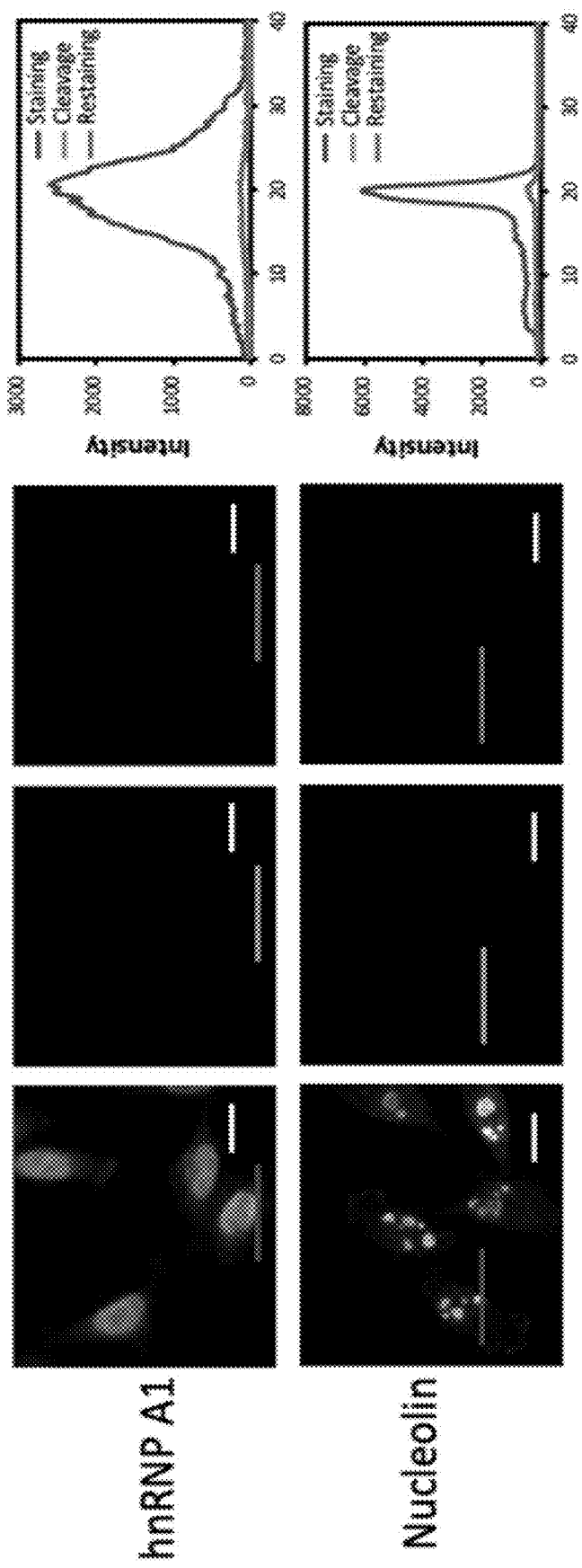
Figure 4, con't.

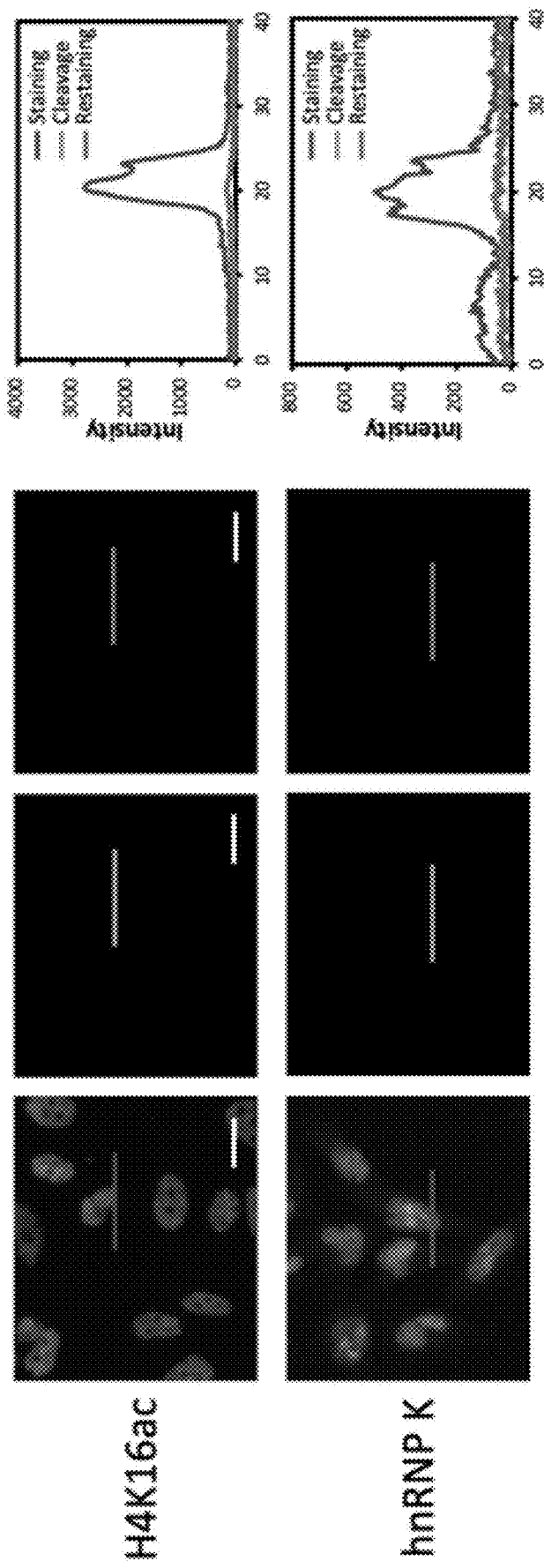
Figure 4, con't.

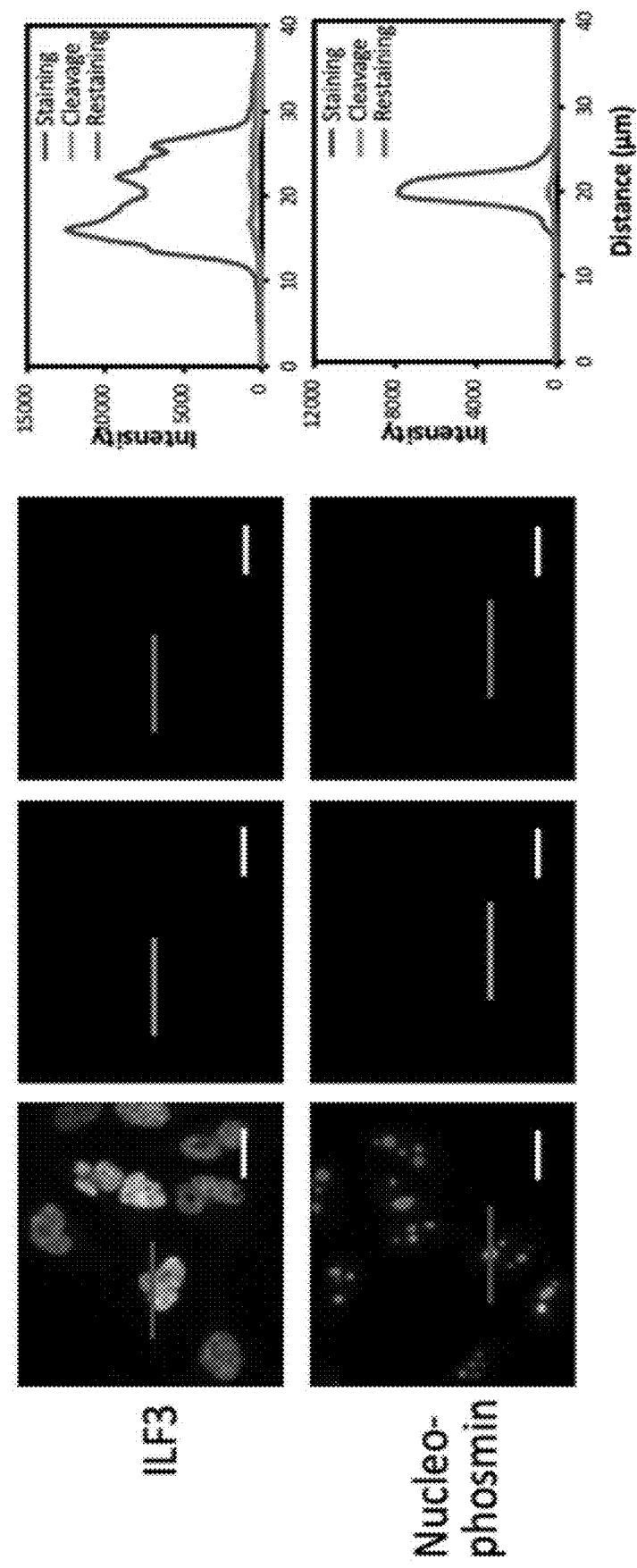
Figure 4, con't.

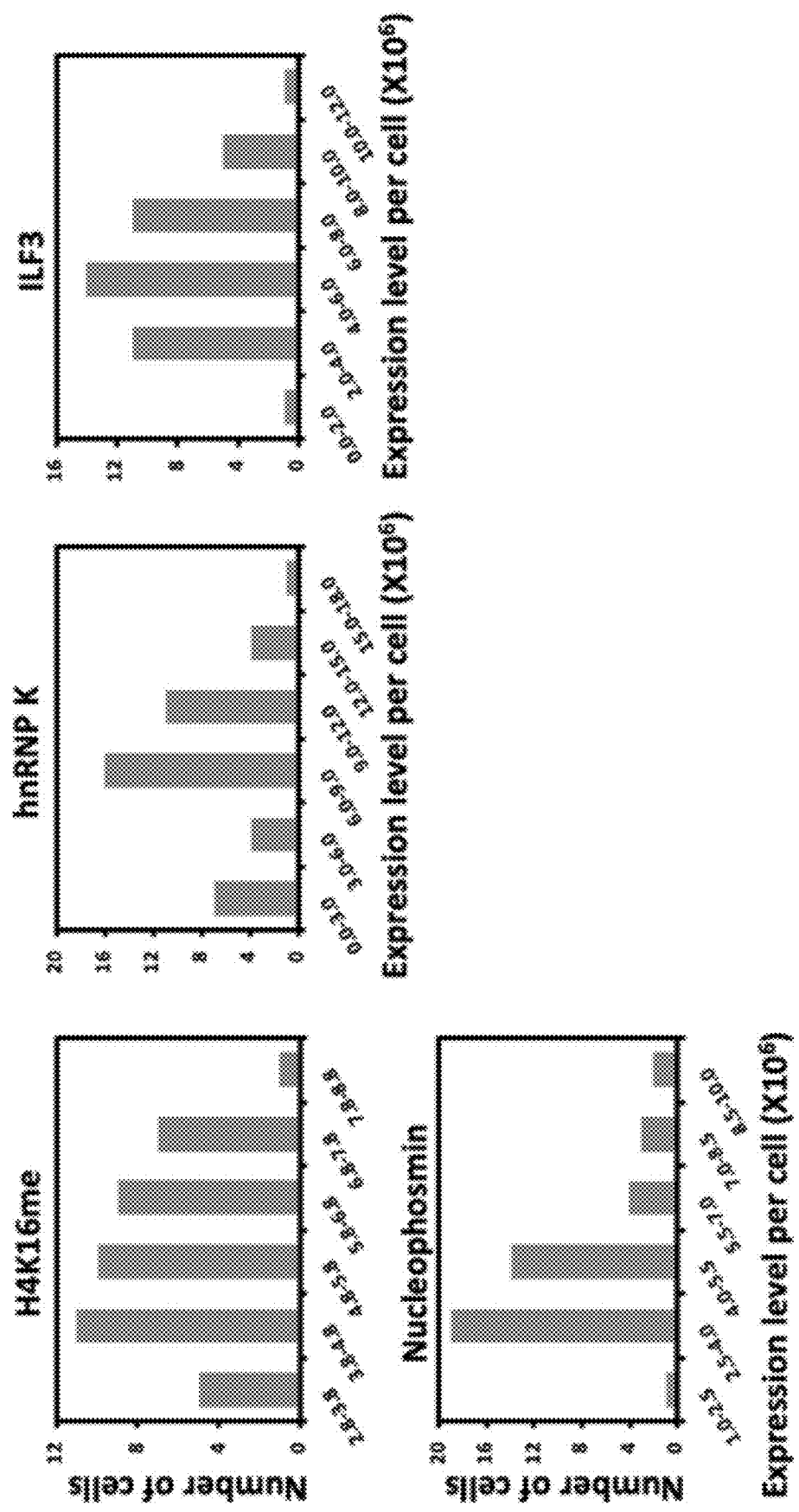
FIG. 7A, con't.

METHODS AND SYSTEMS FOR SENSITIVE AND MULTIPLEXED ANALYSIS OF BIOLOGICAL SAMPLES USING HIGH-PERFORMANCE CLEAVABLE, DETECTABLY-LABELED TYRAMIDE

CROSS-REFERENCE TO RELATED APPLICATIONS

This application claims the benefit of U.S. Application No. 63/162,290, filed on Mar. 17, 2021, the entire content of which is incorporated herein by reference.

STATEMENT REGARDING FEDERALLY SPONSORED RESEARCH

This invention was made with government support under R01 GM127633 awarded by the National Institutes of Health. The government has certain rights in the invention.

BACKGROUND

The ability to comprehensively profile proteins, nucleic acids, and other biomolecules in intact tissue in situ is crucial to understand the molecular mechanisms underlying cancer, neuroscience, and stem cell biology. The differences between individual cells in complex biological systems may have significant consequences in the function and health of the entire systems. The precise location of multiple, varied biomolecules in a tissue or cell is critical for understanding the spatial organization, gene expression regulation, and interactions of diverse cell types in complex multicellular organisms. However, most of the existing methods for in situ analysis of proteins, nucleic acids, and other biomolecules can only quantify a small number of different molecules in a biological sample. Conventional protein imaging methodologies such as immunohistochemistry (IHC) and immunofluorescence (IF) only allow a handful of proteins to be detected in one tissue sample, and the methods may miss transcripts present at low copy numbers. Accordingly, there remains a need in the art for highly sensitive and multiplexed approaches to in situ protein and nucleic acids analysis.

SUMMARY

The present disclosure overcomes the aforementioned drawbacks by providing low-cost, high-throughput, comprehensive, and highly sensitive and high-quality methods for in situ molecular profiling capable of in situ analysis of target biomolecules (e.g., proteins, nucleic acids) in intact tissues with single-molecule sensitivity.

In a first aspect, there is provided herein a cleavable detectably-labeled tyramide (CLT) comprising the compound of Formula (I), wherein R is a detectable marker.

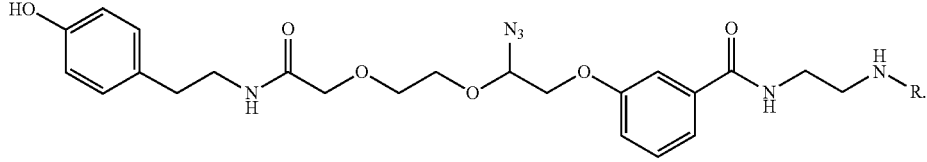

Formula (I)

Exemplary detectable makers include, without limitation, fluorophores, luminescent agents (e.g., chemiluminescent agents), fluorescent proteins, and radioisotopes. By way of example, detectable markers include Cy5, sulfonated cy5, TAMRA (labeled with tetramethylrhodamine or "TMR"), ALEXA FLUOR™ 594, and ATTO 647N and ATTO 700 fluorophores (ATTO-TEC, Germany). Other fluorophores appropriate for use according to the compositions and methods provided herein include, without limitation, quantum dots, ALEXA FLUOR™ 350, ALEXA FLUOR™ 532, ALEXA FLUOR™ 546, ALEXA FLUOR™ 568, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ DYES (e.g., DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800 and the like), Texas Red, and Cy2, Cy3.5, Cy5.5, and Cy7, and sulfonated Cy2, Cy3.5, Cy5, Cy5.5, and Cy7. In some embodiments, the detectable marker is a sulfonated Cy 5, and in some embodiments, there is provided a cleavable detectably-labeled tyramide (CLT) comprising the compound of Formula (II):

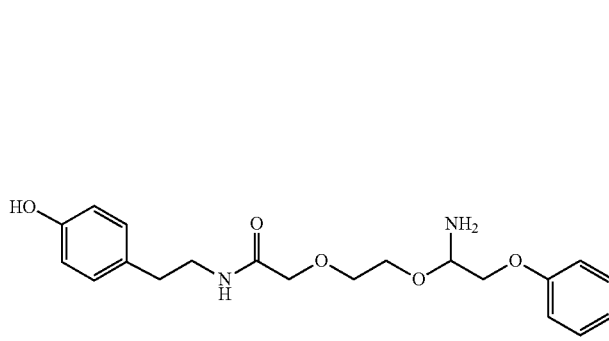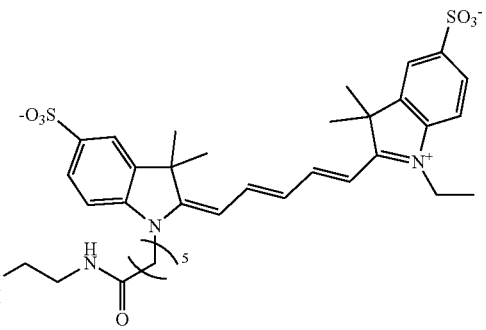

In another aspect, provided herein is a method of multiplexed in situ analysis of biomolecules in a tissue. In some embodiments, the methods comprise or consist essentially of the following steps: (a) contacting the tissue with a plurality of horseradish peroxidase (HRP)-conjugated targeting agents, for example, agents that are configured to specifically bind or hybridize to the target biomolecule in the contacted tissue, wherein the contacting step occurs, e.g., under conditions that promote binding or hybridization of the targeting agents to the target biomolecule; (b) contacting the tissue with the cleavable detectably-labeled tyramide (CLT) compound of Formula I, e.g., under conditions that promote conjugation of the cleavable labeled tyramide to the target biomolecule; (c) imaging the tissue thereby detecting the detectable marker; (d) contacting the tissue sample with a composition comprising 1,3,5-Triaza-7-phosphaadamantane (PTA) and tris(2-carboxyethyl)phosphine (TCEP), e.g., at about 40° C. for about 30 minutes; and (e) repeating steps (a)-(d); wherein a second plurality of HRP-conjugated targeting agents is used to bind to or hybridize to a second target biomolecule, wherein the first and the second target biomolecules are different.

In some embodiments, the method further comprise repeating steps (a)-(d) N times, wherein the Nth plurality of HRP-conjugated targeting agents is used to bind to or hybridize to the Nth target biomolecule, wherein the first through the Nth target biomolecules are different.

The plurality of target biomolecules can comprise proteins, RNA, or DNA, or a combination thereof.

In some embodiments, the CLT comprises the compound of Formula II.

In another aspect, provided herein is a kit for detecting target biomolecules in a cell sample. The kit can comprise or consist essentially of a cleavable detectably-labeled tyramide comprising the compound of Formula I or Formula II, and a written insert component comprising instructions for performing multiplexed in situ analysis of target biomolecules according to methods of this disclosure. In some embodiments, the kit can further comprise a plurality of HRP-conjugated targeting agents configured to bind or hybridize to a target biomolecule. The plurality of HRP-conjugated targeting agents can comprise HRP-conjugated synthetic DNA oligonucleotide probes. The plurality of HRP-conjugated targeting agents can comprise HRP-conjugated polyclonal or monoclonal antibodies, or antigen-binding fragments thereof. The kit can further comprise tris(2-carboxyethyl)phosphine (TCEP), and 1,3,5-Triaza-7-phosphaadamantane (PTA), either as separate components or as a composition, and the written instruction component can further comprise instructions for removing the detectable label from the detectably-labeled tyramide using the TCEP and the PTA.

The foregoing and other advantages of the invention will appear from the following description. In the description, reference is made to the accompanying drawings which form a part hereof, and in which there is shown by way of illustration an embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or patent application file contains at least one drawing in color. Copies of this patent or patent application publication with color drawings will be provided by the Office upon request and payment of the necessary fee.

FIG. 1A-FIG. 1B. (A) Multiplexed in situ protein profiling with high-performance cleavable fluorescent tyramide. After staining protein targets with HRP conjugated antibodies and cleavable fluorescent tyramide, images are captured for protein profiling. Subsequently, a mild chemical reaction is applied to cleave the fluorophores and deactivate HRP simultaneously. Upon reiterative cycles of protein staining, imaging, fluorophore removal and HRP deactivation, multiplexed protein analysis can be achieved in individual cells in situ. (B) Chemical structure of high-performance cleavable fluorescent tyramide, tyramide-$N_3$-Cy5.

FIG. 2A-FIG. 2C. (A) Protein ILF3 in a human tonsil FFPE tissue is stained with tyramide-$N_3$-Cy5. (B) The fluorescence signal is removed by PTA and TCEP. (C) Fluorescence intensity profile corresponding to the red and green line positions in (A) and (B). Scale bars, 10 μm.

Figure 3C:
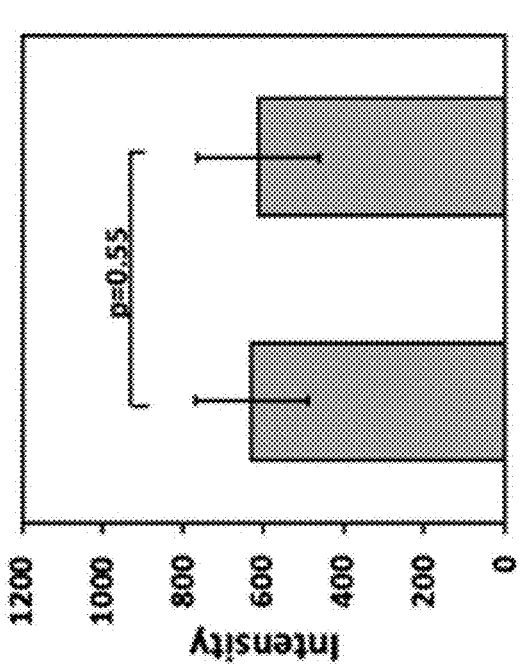
FIG. 3A-FIG. 3C. (A) Protein ILF3 in in a human tonsil FFPE tissue is directly stained with tyramide-$N_3$-Cy5. (B) After the overnight PTA incubation, Protein ILF3 in in a human tonsil FFPE tissue is stained with tyramide-$N_3$-Cy5. (C) Fluorescence intensity of ILF3 staining in (A) and (B) (n=30 positions). Scale bars, 10 μm.

FIG. 8A-FIG. 8D. (A) In the order of increasing expression levels, three proteins are sequentially stained in a human tonsil FFPE tissue. (B) The three proteins are stained by conventional TSA in three different human tonsil FFPE tissues. (C) In the order of decreasing expression levels, the same three proteins are sequentially stained in a human tonsil FFPE tissue. (D) Fluorescence intensity of the three proteins stained in (A), (B) and (C) (n=50 positions). Scale bars, 10 μm.

DETAILED DESCRIPTION

The methods and compositions provided herein are based at least in part on the inventors' development of a highly sensitive and multiplexed in situ protein analysis approach that uses a cleavable labeled tyramide (CLT) comprising Formula I, and which has the potential to quantify numerous different proteins and/or nucleic acids in individual cells of intact tissues at the optical resolution. As described herein, this development provides for in situ analysis of proteins, nucleic acids, and other biomolecules in intact tissues with single-molecule sensitivity.

Accordingly, in a first aspect, provided herein is a cleavable detectably-labeled tyramide. In certain embodiments, a detectable label such as a fluorophore is tethered to tyramide via a cleavable linker. Preferably, the cleavable linker is a chemically cleavable linker. As described herein, to enable signal removal (e.g., fluorescent signal) after protein staining the cleavable detectably labeled tyramide preferably comprises a fluorophore tethered to tyramide through a chemically cleavable linker. An important aspect of the technology of this disclosure is efficient cleavage of the detectable label in a cellular environment while maintaining protein antigenicity. Additionally, the linker may be small enough to permit recognition of CLT by horseradish peroxidase (HRP) and to avoid compromised diffusion of a short-lived tyramide radical. In some embodiments, the cleavable linker comprises the structure of Formula III, wherein R comprises a detectable marker and T comprises tyramide:

Formula III

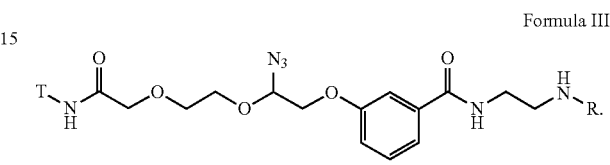

Other cleavable linkers appropriate for use in a CFT of this disclosure include, structures cleaved by enzymes, nucleophiles, electrophiles, reducing reagents, oxidizing reagents, photo-irradiation, metal catalysis, and the like. Further examples of suitable linkers and cleavage mechanisms are described by Milton et al. (U.S. Pat. No. 7,414,116) and by Leriche et al. (*Bioorg. Med. Chem.*, 2012, 20:571-582), which are incorporated herein by reference in their entirety. The linker may be cleavable using a variety of approaches including the addition of a chemical agent, irradiation with one or more wavelengths of light, enzymatic reaction and the like.

In some embodiments, a cleavable detectably-labeled tyramide is tyramide-$N_3$—, having the following chemical structure, Formula (I):

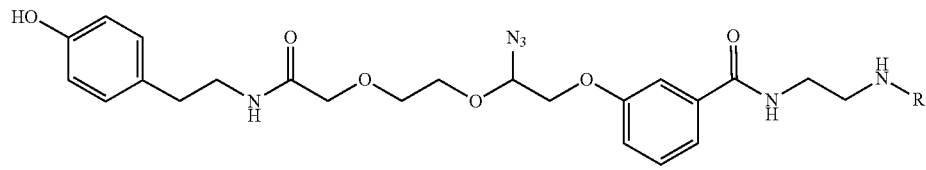

wherein R is a detectable marker.

In some embodiments, the cleavable detectably-labeled tyramide is tyramide-$N_3$-Cy5 of Formula II:

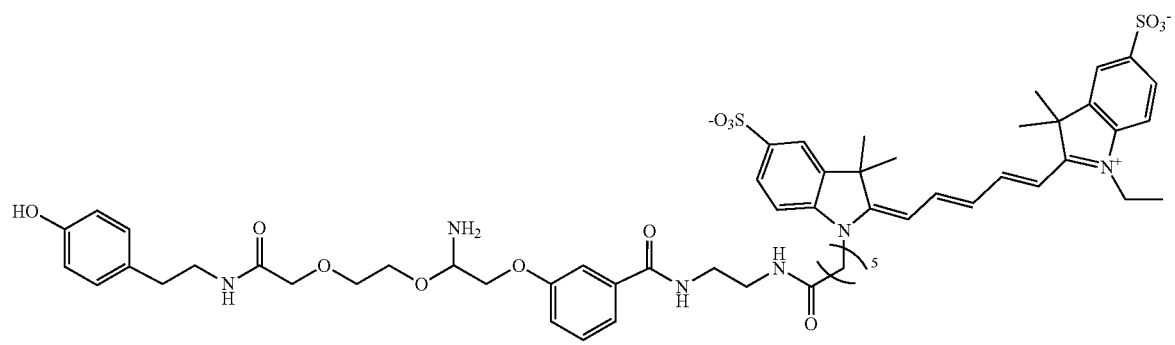

The tyramide-N₃-Cy5 of Formula II was designed and synthesized (FIG. 1B) by tethering fluorophore Cy5 to tyramide through an azide-based cleavable linker. The synthesis and characterization of tyramide-N₃-Cy5 is described in Example 1.

Any appropriate detectable label can be used to produce a cleavable detectably-labeled tyramide. In some embodiments, the detectable label of the cleavable detectably-labeled tyramide is a fluorophore. In such cases, the cleavable detectably-labeled tyramide is cleavable fluorescent tyramide (CFT). Fluorophores useful in the methods of this disclosure include, without limitation, Cy5, TAMRA (labeled with tetramethylrhodamine or "TMR"), ALEXA FLUOR™ 594, and ATTO 647N and ATTO 700 fluorophores (ATTO-TEC, Germany). Other fluorophores appropriate for use according to the methods provided herein include, without limitation, quantum dots, ALEXA FLUOR™ 350, ALEXA FLUOR™ 532, ALEXA FLUO® 546, ALEXA FLUOR™ 568, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ DYES (e.g., DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800 and the like), Texas Red, and Cy2, Cy3.5, Cy5.5, and Cy7, and sulfonated Cy2, Cy3.5, Cy5, Cy5.5, and Cy7. In addition to the use of fluorophores as a detectable moiety, other labels such as luminescent agents (e.g., chemiluminescent agents), fluorescent proteins, and radioisotopes can also be used as detection tags.

In another aspect, provided herein is a method for multiplexed in situ analysis of biomolecules in a tissue. As used herein, the term "multiplexed" refers to the detection of multiple signals (e.g., two or more signals), such as, for example, analytes, fluorescent signals, analog or digital signals, that are combined into one signal over a shared medium. The term encompasses the detection of multiple signals simultaneously in a single sample or single reaction vessel, as well as the combining of images of multiple signals to obtain one image that reflects the combination.

Referring to FIG. 1A, the method comprises three steps in each analysis cycle. First, for analysis of a protein in a tissue, the tissue is contacted with a horseradish peroxidase (HRP)-conjugated antibody configured to bind specifically to the protein target. For analysis of nucleic acids in a tissue, the tissue is contacted with a HRP-conjugated oligonucleotide probe configured to hybridize to the nucleic acid target. In some embodiments, the HRP-conjugated targeting agent is configured to bind directly to the target biomolecule of interest. In some embodiments, the HRP-conjugated targeting agent binds to an intermediate, e.g., binds to a primary antibody or a primary oligonucleotide that binds directly to or hybridizes directly to the target biomolecule.

The tissue is also contacted with a detectably-labeled, cleavable tyramide. HRP catalyzes the coupling reaction between the cleavable tyramide and tyrosine residues on an endogenous protein target in close proximity. In the second step, fluorescence images are captured to generate quantitative protein expression profiles. Finally, detectable labels attached to the cleavable tyramide are chemically cleaved in step that simultaneously deactivates HRP, which allows for initiation of the next analysis cycle. Through reiterative cycles of target staining, fluorescence imaging, fluorophore cleavage, and HRP deactivation, a large number of different target biomolecules with a wide range of expression levels can be quantified in single cells of intact tissues in situ.

In exemplary embodiments, the method comprises (a) contacting the tissue with a plurality of horseradish peroxidase (HRP)-conjugated targeting agents that are configured to specifically bind or hybridize to the target biomolecule in the contacted tissue, wherein the second contacting step occurs under conditions that promote binding or hybridization of the targeting agents to the target biomolecule; (b) contacting the tissue with the cleavable detectably-labeled tyramide (CLT) compound of Formula I, under conditions that promote conjugation of the cleavable labeled tyramide to the target biomolecule; (c) imaging the tissue thereby detecting the detectable marker; (d) contacting the tissue sample with a composition comprising 1,3,5-Triaza-7-phosphaadamantane (PTA) and tris(2-carboxyethyl)phosphine (TCEP) at about 40° C. for about 30 minutes; and (e) repeating steps (a)-(d), as necessary, depending on the number of biomarkers to be detected.

The targeting agent will vary depending on the type of target biomolecule. In some cases, the target biomolecule is a protein or peptide. In such cases, the targeting agent will be an antibody that specifically binds to the target protein or peptide. For example, if the target biomolecule is protein Histone deacetylase 2 (HDAC2), the target agents comprise anti-HDAC2 antibodies conjugated to HRP. Antibodies suitable for the methods include, without limitation, polyclonal antibodies, monoclonal antibodies, and antigen-binding fragments thereof. HRP-conjugated antibodies can be used to detect other target biomolecules such as lipids and metabolites.

In other cases, the target biomolecule is a nucleic acid (e.g., DNA, RNA). In such cases, the targeting agent will be a HRP-conjugated oligonucleotide having sequence complementary to the target nucleic acid sequence. Under appropriate conditions, the HRP-oligonucleotide will hybridize to the target nucleic acid sequence. Upon addition of the CLT, HRP catalyzes a coupling reaction between the tyramide of those CLTs in close proximity with tyrosine residues on endogenous proteins that are also in close proximity. In some cases, multiple cycles of the method are performed to detect multiple target biomolecules using targeting agents that are HRP-conjugated antibodies, HRP-conjugated oligonucleotides, or a combination thereof.

In some cases, the target biomolecule is a carbohydrate. In such cases, the targeting agent can be a HRP-conjugated lectin that is capable of binding carbohydrate. As used herein, the term "lectin" refers to a protein or glycoprotein that binds to specific carbohydrate structures to form a lectin-carbohydrate complex. The term encompasses lectins derived from animal and plant sources, and which bind carbohydrates by affinity. The term "lectin" as used herein also encompasses glycoproteins and proteins not normally termed lectins but which immunologically bind carbohydrates, such as antibodies, e.g., monoclonal antibodies. Since lectins bind selectively to some but not all carbohydrates (e.g., monosaccharides, such as mannose, GleNAc, gelatose, a-fructose or sialic acid) to different degrees, it will be understood that the type of lectin conjugated to HRP will vary depending on the target carbohydrate of interest. Upon addition of the CLT, HRP catalyzes a coupling reaction between the tyramide of those CLTs in close proximity with tyrosine residues on endogenous proteins that are also in close proximity.

Any appropriate method of preparing antibody-horseradish peroxidase conjugates can be used. Exemplary protocols for preparation of an HRP antibody conjugate are known in the art. By way of non-limiting example, HRP can be activated for conjugation by treatment with a 100-fold molar excess of a bifunctional PEG linker having a maleimide group and an active ester group. Antibodies to a protein of interest can be prepared for conjugation by introducing thiols using, for example, DTT. A thiolated antibody can be contacted to a molar excess of HRP comprising a bifunctional PEG linker for conjugation.

Likewise, methods of preparing an oligonucleotide probe conjugated to HRP are well known in the art and can be commercially obtained.

In some cases, the HRP-conjugated detection agent (e.g., antibody, oligonucleotide) and cleavable detectably labeled tyramide are contacted in the presence of a tyramide signal amplification buffer. In some embodiments, the amplification buffer comprises an aqueous phosphate-buffered, borate-buffered, or other buffered solution to which low concentrations of hydrogen peroxide are added. In some embodiments, the amplification buffer comprises 0.0015% $H_2O_2$ and 0.1% triton X-100 in 0.1 M boric acid, pH=8.5. Commercial tyramide signal amplification buffers are available from several manufacturers including, for example, PerkinElmer, ThermoFisher, and Biotium.

In some embodiments, the signal from the detectable marker is removed in a "removing step." In some embodiments, the removing step comprises chemically cleaving the detectable label. Any appropriate means of removing a detectable signal or detectable label (e.g., a fluorophore) can be used according to the methods provided herein. Methods of removal can include without limitation one or more of photobleaching, chemical deactivation, chemical cleavage of the fluorophores (see the Examples below), enzymatic cleavage of the fluorophores, DNA/RNA strand displacement, chemical or heat denaturing of an intermediate fluorescent oligonucleotide, and the like. Since photobleaching can be a time-consuming step, in some cases the methods provided herein comprise efficiently removing fluorescence signals by chemical deactivation or chemical or enzymatic cleavage of detectable labels.

In some embodiments, the methods provided herein comprise chemical inactivation of fluorophores. For example, fluorophores can be inactivated by oxidation. Protocols for oxidation of dyes with hydrogen peroxide, which can be catalyzed using either acidic or basic conditions, or reactive oxygen species (ROS) are known to those practitioners in the art for changing the fluorescent properties of dyes and fluorescent proteins.

In some embodiments, the detectable marker is removed by chemical cleavage of the linker joining the tyramide and the detectable marker. In some embodiments, the linker is cleaved by contacting the sample with tris(2-carboxyethyl) phosphine (TCEP), and 1,3,5-Triaza-7-phosphaadamantane (PTA), either as separate components or as a composition. In some embodiments, the contacted sample is incubated at a temperature of about 30° C., 31°, C32°, 33° C., 34° C., 35° C., 36° C., C37° C., 38° C., 39° C., C40° C., 41° C., 42° C., C43°, 44° C., 45° C., 46° C., 47° C., C48° C., 49° C. or about 50° C. The time of incubation is about 10 to about 120 minutes, 20 to about 90 minutes, 30 to about 60 minutes, or about 30 minutes. In some embodiments, the sample is washed prior to the next cycle.

When fluorescently labeled tyramide is used, fluorescence photomicroscopy can be used to detect and record the results of consecutive in situ analysis using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) *Science* 273:494; Roberts et al. (1999) *Genes Chrom. Cancer* 25:241; Fransz et al. (2002) *Proc. Natl. Acad. Sci. USA* 99:14584; Bayani et al. (2004) *Curr. Protocol. Cell Biol.* 22.5.1-22.5.25; Danilova et al. (2008) *Chromosoma* 117:345; U.S. Pat. No. 6,066,459; and FISH TAG™ DNA Multicolor Kit instructions (Molecular probes) for a review of methods for painting chromosomes and detecting painted chromosomes.

To minimize issues of autofluorescence or background signal, oligonucleotide targeting agents can be designed to hybridize to a target nucleic acid at multiple places on the target nucleic acid sequence. Thus, an increased number of oligonucleotides will hybridize to each target nucleic acid sequence (e.g., transcript) to enhance signal to noise ratio. As used herein, the terms "binding," "to bind," "binds," "bound," or any derivation thereof refers to any stable, rather than transient, chemical bond between two or more molecules, including, but not limited to, covalent bonding, ionic bonding, and hydrogen bonding. The term "binding" encompasses interactions between polypeptides, for example, an antibody and its epitope on a target protein. The term also encompasses interactions between a nucleic acid molecule and another entity such as a nucleic acid or probe element. Specifically, binding, in certain embodiments, includes the hybridization of nucleic acids. In some cases, the methods further comprise a blocking step to reduce background signal. The term "blocking" as used herein refers to treatment of a sample with a composition that prevents the non-specific binding of the target substance to the sample. Typically a blocking composition comprises a protein, such as casein or albumin, and may additionally comprise surfactants. The function of the blocking protein is to bind to the sample to prevent the non-specific binding of assay reagents.

In some cases, the method further comprises a washing step. For example, the method can further comprise washing to remove unhybridized targeting agents and non-specifically hybridized targeting agents prior to the addition of CLT to the sample (e.g., prior to the tyramide-HRP reaction), and prior to visualization. In some embodiments, the methods comprises a washing step after cleaving the detectable label and prior to the next cycle including the addition of a next targeting agent.

The methods of this disclosure can be performed using a tissue sample obtained from any biological entity. The term "biological entity" as used herein means any independent organism or thing, alive or dead, containing genetic material (e.g., nucleic acid) that is capable of replicating either alone or with the assistance of another organism or cell. Sources for nucleic acid-containing biological entities include, without limitation, an organism or organisms including a cell or cells, bacteria, yeast, fungi, algae, viruses, or a sample thereof. Specifically, an organism of the current disclosure includes bacteria, algae, viruses, fungi, and mammals (e.g., humans, non-human mammals). The methods and compositions described herein can be performed using a variety of biological or clinical samples comprising cells that are in any (or all) stage(s) of the cell cycle (e.g., mitosis, meiosis, interphase, G0, G1, S and/or G2). As used herein, the term "sample" include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. In some cases, samples are obtained by swabbing, washing, or otherwise collecting biological material from a non-biological object such as a medical device, medical instrument, handrail, door knob, etc. Samples are prepared for assays of this disclosure using conventional techniques, which typically depend on the source from which a sample or specimen is taken. These examples are not to be construed as limiting the sample types applicable to the methods and/or compositions described herein.

In some embodiments, the methods provided herein comprise a cell or tissue fixation step. For example, the cells of a biological sample (e.g., tissue sample) can be fixed (e.g., using formalin, formaldehyde, or paraformaldehyde fixation techniques known to one of ordinary skill in the art). In some cases, the tissue is formalin-fixed and paraffin-embedded (FFPE). Any fixative that does not affect antibody binding or nucleic acid hybridization can be utilized in according to the methods provided herein. In other cases, the methods are performed on unfixed ("fresh") tissue samples.

As described herein, the methods of the present invention provide for multiplexed in situ analysis of biomolecules in a tissue. Through consecutive cycles of targeting agent binding/hybridization, fluorescence imaging, and signal removal, different biomolecule species can be identified as fluorescent spots with unique color sequences. In some embodiments, the CTL's of different cycles, which are used in conjunction with different targeting agents, comprise different labels. For example, in a first cycle, a first targeting agent is hybridized to a first target biomolecule, and a first CTL comprising a first detectable label is used. In a subsequent cycle, an second targeting agent is hybridized to a second target biomolecule, and a second CTL comprising a second detectable label is used.

As used herein, the term "biomolecule" or "biological molecule" refers to any molecule that is substantially of biological origin and encompasses proteins, peptides, and nucleic acids. Such molecules may include non-naturally occurring components that mimic a naturally occurring component, e.g., a non-naturally occurring amino acid. The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. As used herein, the terms "nucleic acid" or "oligonucleotide" refer to and encompass any physical string or collection of monomer units (e.g., nucleotides) that can connect to form a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the nucleic acid can be deoxyribonucleotides, ribonucleotides or nucleotide analogs, and can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The nucleic acid can additionally comprise non-nucleotide elements such as labels, quenchers, blocking groups, or the like. The nucleic acid can be single-stranded or double-stranded.

As used herein, the terms "nucleic acid of interest," and "target nucleic acid" include a nucleic acid originating from one or more biological entities within a sample. The target nucleic acid of interest to be detected in a sample can be a sequence or a subsequence from DNA, such as nuclear or mitochondrial DNA, or cDNA that is reverse transcribed from RNA in the sample. The sequence of interest can also be from RNA, such as mRNA, rRNA, tRNA, miRNA, siRNAs, antisense RNAs, or long noncoding RNAs. More generally, the sequences of interest can be selected from any combination of sequences or subsequences in the genome or transcriptome of a species or an environment. In some cases, a defined set of targeting agents are oligonucleotide probes that are designed to hybridize to the plurality of sequences that would be expected in a sample, for example a genome or transcriptome, or a smaller set when the sequences are known and well-characterized, such as from an artificial source.

Oligonucleotide probes useful for the methods provided herein are of any length sufficient to permit probe penetration and to optimize hybridization of probes for in situ analysis according to the methods of this disclosure. Preferably, probe length is about 20 bases to about 500 bases. As probe length increases, so increases the number of binding sites that can be incorporated into a given probe for hybridization to the probe of the following cycle as well as the signal to noise ratio. However, longer than 500 bases, the probes may not efficiently penetrate the cellular membrane. Preferably, the oligonucleotide probes have a probe length between 20 and 500 nucleotides, 20 and 250, 50 and 250, 150 and 250 nucleotides, 20 and 150, or 50 and 150 nucleotides, inclusive.

The terms "hybridize" and "hybridization" as used herein refer to the association of two nucleic acids to form a stable duplex. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, N.Y.). One of skill in the art will understand that "hybridization" as used herein does not require a precise base-for-base complementarity. That is, a duplex can form, between two nucleic acids that contained mismatched base pairs. The conditions under which nucleic acids that are perfectly complementary or that contain mismatched base pairs will hybridize to form a duplex are well known in the art and are described, for example, in MOLECULAR CLONING: A LABORATORY MANUAL, $3^{rd}$ ed., Sambrook et al., eds., Cold Spring Harbor Press, Cold Spring Harbor (2001) at Chapter 10, which is herein incorporated by reference. As used herein, the term "complementary" refers to a nucleic acid that forms a stable duplex with its "complement". For example, nucleotide sequences that are complementary to each other have mismatches at less than 20% of the bases, at less than about 10% of the bases, preferably at less than about 5% of the bases, and more preferably have no mismatches.

Kits

In another aspect, provided herein is a kit comprising reagents for performing multiplexed in situ analysis of biomolecules in a tissue. Preferably, the kit comprises a cleavable detectably-labeled tyramide of Formula I or Formula II, and a written insert component comprising instructions for performing multiplexed in situ analysis of target biomolecules according to the methods provided herein. In some embodiments, the kit further comprises a one or more HRP-conjugated targeting agents configured to bind or hybridize to a target biomolecule. As described herein, the targeting agents can be synthetic DNA oligonucleotide probes, polyclonal antibodies, monoclonal antibodies, antigen-binding fragments of an antibody, or some combination thereof. In some embodiments, the plurality of HRP-conjugated targeting agents comprises HRP-conjugated synthetic DNA oligonucleotide probes. In some embodiments, the plurality of HRP-conjugated targeting agents comprises HRP-conjugated polyclonal or monoclonal antibodies, or antigen-binding fragments thereof. In some embodiments, the kit further comprises an amplification reaction buffer, a blocking reagent, and/or a hydrogen peroxide additive.

In some embodiments, the detectable maker includes, without limitation, fluorophores, luminescent agents (e.g., chemiluminescent agents), fluorescent proteins, and radio-isotopes. By way of example, detectable markers include Cy5, sulfonated cy5, TAMRA (labeled with tetramethylrhodamine or "TMR"), ALEXA FLUOR™ 594, and ATTO 647N and ATTO 700 fluorophores (ATTO-TEC, Germany). Other fluorophores appropriate for use according to the compositions and methods provided herein include, without limitation, quantum dots, ALEXA FLUOR™ 350, ALEXA FLUOR™ 532, ALEXA FLUOR™ 546, ALEXA FLUOR™ 568, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ DYES (e.g., DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800 and the like), Texas Red, and Cy2, Cy3.5, Cy5.5, and Cy7, and sulfonated Cy2, Cy3.5, Cy5, Cy5.5, and Cy7. In some embodiments, the detectable marker is a sulfonated Cy 5, and in some embodiments, there is provided a cleavable detectably-labeled tyramide (CLT) comprising the compound of Formula (II)

In some embodiments, the kit includes instructions for employing the kit components as well the use of any other reagent not included in the kit. Instructions may include variations that can be implemented. In some embodiments, the kit further comprises tris(2-carboxyethyl)phosphine (TCEP) and 1,3,5-Triaza-7-phosphaadamantane (PTA) either as separate components or as a composition. In such cases, the written instruction component further comprises instructions for removing the detectable label from the detectably-labeled tyramide using the TCEP/PTA.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As used herein and in the appended claims, the singular forms "a", "an" and "the" include plural reference, unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. In addition, the terms "comprising", "including" and "having" can be used interchangeably.

As used herein, "about" means within 5% of a stated concentration range or within 5% of a stated time frame.

Various embodiments and aspects of the present invention as delineated hereinabove and as claimed in the claims section below find experimental support in the following examples which, together with the above descriptions, illustrate some embodiments of the invention in a non-limiting fashion.

EXAMPLES

Example 1: Multiplexed In Situ Protein Profiling with High-Performance Cleavable Fluorescent Tyramide Abstract: Understanding the composition, function and regulation of complex cellular systems require tools that quantify the expression of multiple proteins at their native cellular context. Here, we report a highly sensitive and accurate protein in situ profiling approach using off-the-shelf antibodies and cleavable fluorescent tyramide (CFT). In each cycle of this method, protein targets are stained with horseradish peroxidase (HRP) conjugated antibodies and CFT. Subsequently, the fluorophores are efficiently cleaved by mild chemical reagents, which simultaneously deactivate HRP. Through reiterative cycles of protein staining, fluorescence imaging, fluorophore cleavage, and HRP deactivation, multiplexed protein quantification in single cells in situ can be achieved. We designed and synthesized the high-performance CFT, and demonstrated that over 95% of the staining signals can be erased by mild chemical reagents while preserving the integrity of the epitopes on protein targets. Applying this method, we explored the protein expression heterogeneity and correlation in a group of genetically identical cells. With the high signal removal efficiency, this approach also enables us to accurately profile proteins in formalin-fixed paraffin-embedded (FFPE) tissues in the order of low to high and also high to low expression levels.

Introduction: Highly multiplexed protein profiling in their native spatial contexts holds great promise to reveal the composition, regulation and interaction of the various cell types in complex cellular systems [1,2]. Protein microarray [3] and mass spectrometry [4] are well-established methods for proteomic analysis. However, as these approaches do not quantify proteins in their original cellular environment, the location information of the proteins are lost during analysis. Immunofluorescence is a powerful tool for in situ protein quantification. Nonetheless, due to the spectral overlap of the common fluorophores, immunofluorescence only allows a small number of varied proteins to be profiled on each specimen [5].

To allow multiplexed in situ protein analysis, several techniques [6-14] have been explored. In these approaches, the fluorophores or metal isotopes directly conjugated antibodies are applied as detections tags. Without further signal amplification, these approaches suffer from low detection sensitivity, which limits their applications for analysis of low expression proteins or studying highly autofluorescent specimen, such as formalin fixed, paraffin embedded (FFPE) tissues [7]. Recently, some signal amplification methods have been developed for multiplexed protein imaging [15, 16]. However, these approaches require a chemical or oligonucleotide tag to be conjugated to primary antibodies. To prepare those tag conjugated primary antibodies can be time-consuming and expensive. More importantly, the bulky chemical or oligonucleotide tag can interfere with the binding affinity and specificity of the primary antibodies.

To enable highly sensitive and multiplexed protein imaging with off-the-shelf antibodies, our group developed a reiterative protein staining approach using cleavable fluorescent tyramide (CFT) [17]. We demonstrated its sensitivity is improved by about two orders of magnitude compared with other existing methods. As a result, its imaging time is dramatically reduced, and the sample throughput is significantly enhanced. However, some non-ideal factors still exist. For example, the carbamate group in the first-generation CFT could potentially react with the nucleophiles in the cellular environment or during storage, which may lead to side reactions or short shelf life. Additionally, with tris(2-carboxyethyl)phosphine (TCEP) as the signal removal reagent, the first-generation CFT requires 65° C. to remove ~95% of the staining signals. Nevertheless, this relatively high reaction temperature could damage the integrity of the epitopes [17].

Here, we report a highly sensitive and multiplexed in situ protein analysis method using high-performance CFT. In this approach, protein targets are recognized by antibodies conjugated with horseradish peroxidase (HRP) and then stained with CFT. Without the carbamate group in this newly designed CFT, it avoids the potential side reactions with the cellular nucleophiles. Additionally, over 95% the staining signals can be efficiently removed using 1,3,5-Triaza-7-phosphaadamantane (PTA) and TCEP at 40° C. And simultaneously, HRP is also effectively deactivated under this mild condition. Through reiterative cycles of target staining, fluorescence imaging, signal erasing and HRP quenching, we demonstrated at least 10 reiterative immunofluorescence cycles can be successfully carried out in cultured cells. With the generated multiplexed single-cell in situ protein profiling data, we explored the protein expression heterogeneity and correlation in a population of genetically identical cells. We also showed the significantly improved signal removal efficiency of our approach enables the accurate quantification of multiple proteins in the order of low to high and also high to low expression levels in FFPE tissues.

1. Materials and Methods

1.1 General Information

Chemicals and solvents were purchased from Sigma-Aldrich, and were used directly without further purification. Bioreagents were purchased from Invitrogen, unless otherwise noted.

1.2 Synthesis of Tyramide-$N_3$-Cy5

Cy5-$N_3$ acid (8.3 µmol), prepared according to the literature [18], N,N,N',N'-Tetramethyl-O—(N-succinimidyl)uronium tetrafluoroborate (TSTU) (12.5 mg, 41.5 µmol) and N,N-diisopropylethylamine (DIPEA) (7.3 µL, 41.5 µmol) was mixed in anhydrous DMF (300 µL) and stirred at room temperature. The complete transformation of Cy5-$N_3$ acid into Cy5-$N_3$ NHS ester was observed via TLC (DCM:Methanol=5:1) after 30 minutes. Then, tyramine hydrochloride (6.23 mg, 41.5 µmol) and DIPEA (14.6 µL, 83.0 µmol) were added into the reaction mixture and stirred for 2 hours. The solvent was evaporated, and the solid residue was purified by preparative TLC (DCM:Methanol=5:1) to obtain the product as dark blue solid. tyramide-$N_3$-Cy5 was further purified by semi preparative reversed phase HPLC [HPLC gradient: A, 100% 0.1 M TEAA; B 100% MeCN; 0-2 min, 5% B (flow 2-5 ml/min); 2-10 min, 5-22% B (flow 5 ml/min); 10-15 min, 22-30% B (flow 5 ml/min); 15-20 min, 30-40% B (flow 5 ml/min); 20-25 min, 40-50% B (flow 5 ml/min); 25-30 min, 50-60% B (flow 5 ml/min); 30-32 min, 60-70% B (flow 5 ml/min); 32-35 min, 70-95% B (flow 5 ml/min); 35-37 min, 95% B (flow 5 ml/min); 37-39 min, 95-5% B, (flow 5 ml/min); 39-42 min, 5% B (flow 5-2 ml/min)]. The fraction with retention time of 26.4 minutes was collected. After evaporating all the solvents, the residue was co-evaporated with methanol twice to obtain pure tyramide-$N_3$-Cy5 as blue solid (3.53 mg, 3.10 µmol). $^1$H NMR [500 MHz MeOD]: 8.25 (2H, $SO_3H$, t, J=16.5 Hz), 7.90 (4H, Ar—H, m), 7.35-7.10 (5H, Ar—H, m), 6.95 (1H, Ar—H, m), 6.9 (2H, Ar—H, d, J=10.5 Hz), 6.62-6.52 (3H, 2×Ar—H and CH=, m), 6.27-6.14 (2H, CH=, dd, J=17 Hz, J=8.0 Hz), 4.7 (1H, CH—$N_3$, t, J=8.0 Hz), 4.10-3.96 (4H, 2×$CH_2$N, m), 3.90 (2H, $OCH_2$, t, J=9.0 Hz), 3.84-3.77 (3H, $OCH_2$, Hb and $CH_2$C(O), m), 3.65-3.60 (1H, $OCH_2$, Ha, m), 3.53 (2H, $CH_2$N, t, J=7.5 Hz), 3.37 (2H, $CH_2$N, t, J=5.0 Hz), 3.29 (2H, $CH_2$O, t, J=5.0 Hz), 2.57 (2H, $CH_2$N, t, J=9.0 Hz), 2.13-2.01 (4H, $CH_2$ and $CH_2$C(O), m), 1.65-1.52 (15H, 4×$CH_3$ and $CH_3$, m), 1.33-1.24 (6H, 3×$CH_2$, m). HRMS (ESI–, m/z) calculated for $C_{57}H_{71}N_8O_{13}S_2$ [(M–2H)⁻]: 1137.4529, found: 1137.4327.

1.3 Deparaffinization and Antigen Retrieval of FFPE Tonsil Tissue

An FFPE Tonsil tissue was heated at 60° C. for 1 h before being deparaffinized in xylene 5 times, each for 4 minutes. Afterwards, the slide was immersed in 100% ethanol for 4 minutes twice, 95% ethanol for 4 minutes, 75% ethanol for 4 minutes then rinsed with DI water. Heat induced antigen retrieval (HIAR) was performed on the slide by using the microwave. The slide was immersed in antigen retrieval buffer (diluted 100 times from Abcam 100× Citrate Buffer pH 6.0 with DI water) and heated in the microwave for 2 minutes and 40 seconds at level 10 setting and then for 14 minutes at level 2 setting. After cooling down for 20 minutes, the slide was rinsed with DI water.

1.4 Protein Staining in FFPE Tonsil Tissue

To deactivate the endogenous peroxidase, the slide was incubated with 3% $H_2O_2$ for 10 minutes at room temperature, followed by 3 times washes using 1×PBT in PBS. Next, the slide was incubated with 1× blocking buffer for 30 min at room temperature. Then, the slide was incubated with 5 µg/mL rabbit anti hnRNP K, HRP (Abcam; ab204456) in antibody blocking buffer for 1 h, and washed 3 times with 1×PBT, each for 5 min. The slide was stained with tyramide-$N_3$-Cy5 at the concentration of 10 nmol/mL in amplification buffer for 7 minutes at room temperature, then washed 3 times with 1×PBT, each for 5 minutes. The stained tissue was incubated with GLOX buffer (10 mM Tris HCl and 0.4% glucose in 2× saline-sodium citrate (SSC) buffer (30 mM trisodium citrate, 300 mM sodium chloride, pH=7.0)) at room temperature for 1 min, and subsequently imaged in GLOX solution (1% catalase and 0.37 mg/mL glucose oxidase in GLOX buffer).

1.5 Fluorophore Cleavage and HRP Deactivation

The stained tissue was incubated with 100 mM 1,3,5-Triaza-7-phosphaadamantane (PTA) and 100 mM tris(2-carboxyethyl)phosphine (TCEP) sequentially at 40° C., each for 30 minutes. After 5 min wash with PBT and 1×PBS, each for 3 times, the tissue was imaged in GLOX solution.

1.6 Effect of Cleavage by PTA

After deparaffined and antigen retrieved, an FFPE tonsil tissue was incubated with 100 mM PTA overnight at 40° C. Then, the slide was washed 3 times with 1×PBT, each for 5 min. Subsequently, the slide was incubated with 5 µg/mL rabbit anti ILF3, HRP (Abcam; ab206250) and stained with tyramide-$N_3$-Cy5. In the control experiment, without PTA treatment in advance, another FFPE tonsil tissue was directly stained with rabbit anti ILF3, HRP (Abcam; ab206250) and tyramide-$N_3$-Cy5.

1.7 Cell Culture

HeLa CCL-2 cells (ATCC) were maintained in a humidified atmosphere with 5% $CO_2$ at 37° C. in Dulbelcco's modified Eagle's Medium (DMEM), which was supplemented with 100 U/mL penicillin, 100 g/mL streptomycin and 10% fetal bovine serum. Cells plated on chambered coverglass (200 µL medium/chamber) (Thermo Fisher Scientific) were allowed to reach ~60% confluency in 1 to 2 days.

1.8 Cell Fixation and Permeabilization

Cultured HeLa cells were fixed with 4% formaldehyde (Polysciences) in 1× phosphate buffered saline (PBS) (pH=7.4) for 15 min at 37° C. Subsequently, the cells were washed with 1×PBS three times, each for 5 min. After permeabilized with PBT (0.1% Triton-X 100 in 1×PBS) at room temperature for 10 min, cells were washed with 1×PBS three times, each for 5 min.

1.9 Immunofluorescence with CFT

To block endogenous peroxidase, fixed and permeabilized HeLa cells were incubated with 0.15% $H_2O_2$ in PBT for 10 min, and subsequently washed three times with 1×PBS, each for 5 min. Then, the cells were blocked with 1× blocking buffer (0.1% (vol/vol) Triton X-100, 1% (wt/vol) bovine serum albumin and 10% (vol/vol) normal goat serum) for 1 h at room temperature. Subsequently, the cells were incubated with 5 µg/mL HRP conjugated primary antibodies in 1× blocking buffer for 1 h, followed by 3 times wash with PBT, each for 5 min. Then, the cells were incubated with tyramide-$N_3$-Cy5 at the concentration of 10 nmol/mL in amplification buffer (0.1 M Boric acid, pH=8.5) for 7 min. Afterwards, the cells were washed quickly with PBT twice, and then washed with PBT again for 3 times, each for 5 min. The stained cells were incubated with GLOX buffer (10 mM Tris HCl and 0.4% glucose in 2× saline-sodium citrate (SSC) buffer (30 mM trisodium citrate, 300 mM sodium chloride, pH=7.0)) at room temperature for 1 min, and subsequently imaged in GLOX solution (1% catalase and 0.37 mg/mL glucose oxidase in GLOX buffer). The primary antibodies used in this work include rabbit anti-HMGB1, HRP (Thermo Fisher Scientific; PA5-22722), rabbit anti-HDAC2, HRP (Abcam; ab195851), rabbit anti-TDP43, HRP (Abeam; ab193850), rabbit anti-PABPN1, HRP (Abeam; ab207515), rabbit anti-hnRNP A1, HRP (Abeam; ab198535), mouse anti-Nucleolin, HRP (Abeam; ab198492), rabbit anti-Histone H4 (acetyl K16), HRP (Abeam; ab200859), mouse anti-hnRNP K, HRP (Abeam; ab204456), rabbit anti-ILF3, HRP (Abeam; ab206250) and mouse anti-Nucleophosmin, HRP (Abeam; ab202579).

1.10 Multiplexed Protein Imaging in Cells

Fixed and blocked HeLa cells were incubated with HRP conjugated antibodies at the concentration of 5 µg/mL for 1 h at room temperature, and subsequently stained with tyramide-$N_3$-Cy5. Afterwards, the stained cells were imaged and then incubated with 100 mM PTA and 100 mM TCEP sequentially at 40° C., each for 30 minutes. The cells were imaged again, followed by the next cycle of immunofluorescence. The sequentially applied antibodies include rabbit anti-HMGB1, HRP (Thermo Fisher Scientific; PA5-22722), rabbit anti-HDAC2, HRP (Abeam; ab195851), rabbit anti-TDP43, HRP (Abeam; ab193850), rabbit anti-PABPN1, HRP (Abeam; ab207515), rabbit anti-hnRNP A1, HRP (Abeam; ab198535), mouse anti-Nucleolin, HRP (Abeam; ab198492), rabbit anti-Histone $H_4$, HRP (acetyl K16) (Abeam; ab200859), mouse anti-hnRNP K, HRP (Abeam; ab204456), rabbit anti-ILF3, HRP (Abeam; ab206250) and mouse anti-Nucleophosmin, HRP (Abeam; ab202579). In control experiments, fixed and blocked HeLa cells were incubated with HRP conjugated primary antibodies at the concentration of 5 µg/mL for 1 h at room temperature, and subsequently stained with Cy5-tyramide (PerkinElmer).

1.11 Multiplexed Protein Imaging in FFPE Tonsil Tissue

After deparaffinization and antigen retrieval, the endogenous peroxidase in FFPE tonsil tissues were blocked by 3% $H_2O_2$. Subsequently, the slide was incubated with HRP conjugated antibodies at the concentration of 5 µg/mL for 1 h at room temperature, and then stained with tyramide-$N_3$-Cy5. Afterwards, the stained tissues were imaged and then incubated with 100 mM PTA and 100 mM TCEP sequentially at 40° C., each for 30 minutes. The tissues were imaged again, followed by the next cycle of immunofluorescence. The antibodies, rabbit anti-ILF3, HRP (Abeam; ab206250), mouse anti-Nucleophosmin, HRP (Abeam; ab202579) and mouse anti-hnRNP K, HRP (Abeam; ab204456), were applied in the forward and reverse orders on two different slides.

1.12 Imaging and Data Analysis

The HeLa cells and FFPE tonsil tissues were imaged using a Nikon Ti-E epifluorescence microscope with a 20× objective, Chroma filter 49009 and a CoolSNAP HQ2 camera. Image analysis was performed with NIS-Elements Imaging software.

2. Results

2.1 Platform Design

In this multiplexed protein imaging approach, each staining cycle is composed of three major steps (FIG. 1A). First, the protein of interest is recognized by over-the-shelf antibodies labeled with HRP, which catalyzes the coupling reaction between the tyramide in CFT and the tyrosine residues on the proteins proximal to the antibodies. Second, the specimen is imaged under a fluorescence microscope to generate quantitative single-cell in situ protein expression profiles. In the last step, the fluorophores tethered to tyramide are efficiently removed by chemical cleavage, and HRP is simultaneously deactivated. With continuous cycles of staining, imaging, cleavage and HRP deactivation, highly multiplexed and sensitive protein profiling can be achieved in single cells in situ.

2.2. Design and Synthesis of High Performance CFT

To eliminate the potential side reactions with the cellular nucleophiles and also improve the shelf life, the high-performance CFT should avoid the carbamate group. Additionally, the linker tethering the fluorophore and tyramide must be cleaved efficiently under a mild condition by a bioorthogonal reaction. Our group recently has developed cleavable fluorescent oligonucleotide for comprehensive RNA and DNA in situ profiling [18]. The azide-based linker used in that method satisfies the two requirements for successful CFT. Therefore, that linker is applied to couple the fluorophore to tyramide in high performance CFT. Most tissues exhibit stronger autofluorescence in the green and yellow emission channels than in the red channel [19]. Thus, to minimize the impact of autofluorescence on the accurate protein analysis, we applied Cy5 as the fluorophore in CFT under the current study.

To synthesize the designed tyramide-$N_3$-Cy5 (FIG. 1B), Cy5 NHS ester was first coupled the azide-based linker, as previously reported in the literature. The generated product was subsequently converted into the NHS ester and conjugated with tyramine. The prepared CFT was purified by high performance liquid chromatography (HPLC) and characterized by nuclear magnetic resonance (NMR) spectroscopy and mass spectrometry.

2.3. Efficient Fluorophore Cleavage while Preserving Epitope Integrity

One of the critical requirements for the success of the multiplexed protein imaging approach is to efficiently remove the staining signals without loss of protein antigeneity. In this way, the signal leftover generated in the previous cycles can be minimized, and other protein targets can still be successfully recognized by antibodies in the following immunofluorescence cycles. To assess the fluorophore cleavage efficiency of the high-performance CFT, we stained protein ILF3 in a human tonsil FFPE tissue (FIG. 2A). To facilitate the efficient signal removal in different microenvironment, we applied the positively charged phosphine PTA in combination with the negatively charged phosphine TCEP to perform fluorophore cleavage. After incubating with PTA and TCEP at 40° C. for 30 min, over 95% of the signals were removed (FIG. 2B, C). Compared with the first-generation CFT, the reaction temperature of 65° C. is required to achieve the similar cleavage efficiency. However, that high cleavage temperature leads to the partial loss of protein antigeneity. The results here suggest that the fluorophore in the high-performance CFT can be very efficiently removed under a relatively low cleavage temperature.

Figure 3B:
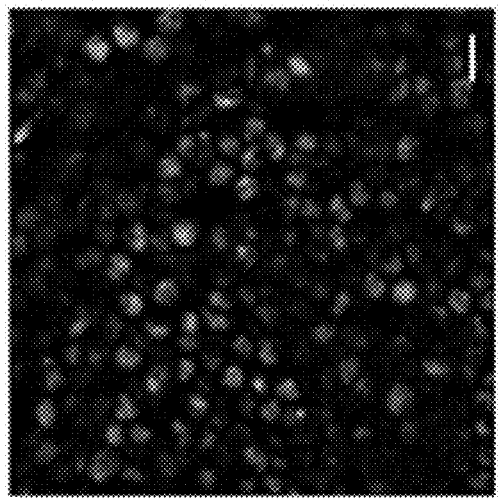
Figure 3A:
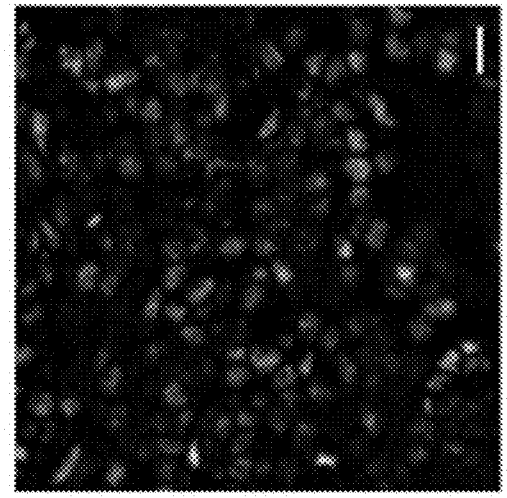

We next investigated whether the epitope integrity is preserved under this cleavage condition. Previously, we have shown that the TCEP treatment at this relatively low temperature does not result in loss of protein antigeneity [8]. Thus, here we evaluated the effects of the PTA incubation on the epitope integrity (FIG. 3). After the PTA treatment overnight, protein ILF3 was stained in a human tonsil FFPE tissue. The generated staining patterns (FIG. 3A, B) and signal intensities (FIG. 3C) are consistent with the ones obtained without the PTA treatment. These results indicate that the antibody antigeneity is maintained under our mild fluorophore cleavage condition.

2.4. Simultaneous HRP Deactivation and Fluorophore Cleavage

Figure 4:
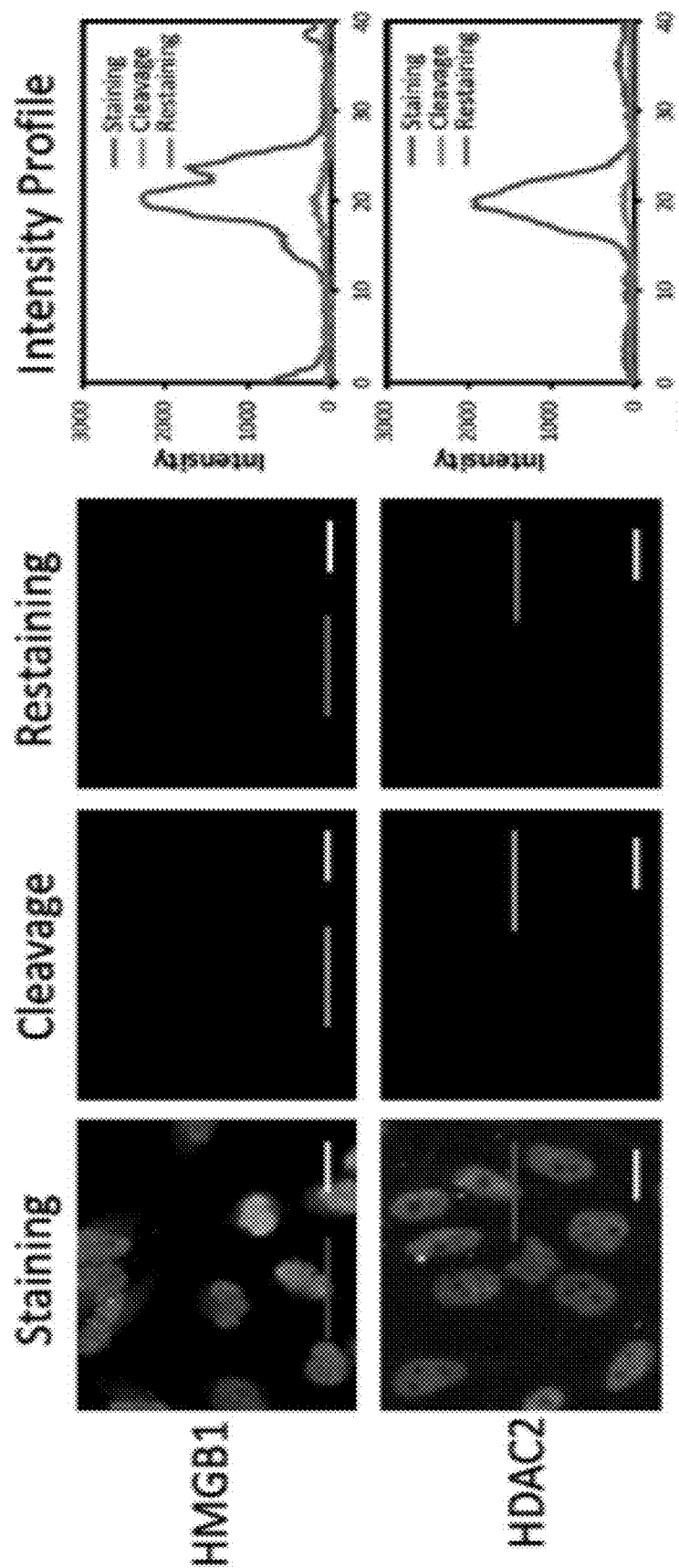
FIG. 4. Ten proteins in HeLa cells are stained with tyramide-$N_3$-Cy5 (the first column). Subsequently, the staining signals are removed by PTA and TCEP (the second column). Then, the cells are re-incubated with tyramide-$N_3$-Cy5 (the third column). The fourth column shows the signal intensity profiles corresponding to the red, orange and green line positions in the first three columns. Scale bars, 15 μm.

To enable accurate protein expression analysis by this reiterative imaging approach, it also requires the HRP on antibodies to be deactivated after the staining images have been captured in each analysis cycle. In this way, the HRP applied in the previous cycles will not produce false positive signals in the following cycles. To evaluate whether PTA and TCEP can cleavage the fluorophore and deactivate HRP simultaneously, we stained HMGB1, HDAC2, TAP43, PABPN1, hnRNP A1, Nucleolin, H4K16ac, hnRNP K, ILF3 and Nucleophosmin with HRP labeled antibodies and the high-performance tyramide-$N_3$-Cy5 in HeLa cells (FIG. 4). All the antibodies used in this study are well validated and documented in the literatures [20-29]. With the PTA and TCEP treatment, over 95% of the staining signals were erased, leading to the on/off ratio of about 20:1. After signal removal, we stained the cells again with tyramide-$N_3$-Cy5. No signal increases were observed for all the 10 proteins. These results confirm that PTA and TCEP can efficiently cleave the fluorophores in the high-performance CFT, and also suggest that HRP are almost completely deactivated simultaneously.

2.5. Multiplexed Protein Imaging in Cultured Cells

Figure 5A:
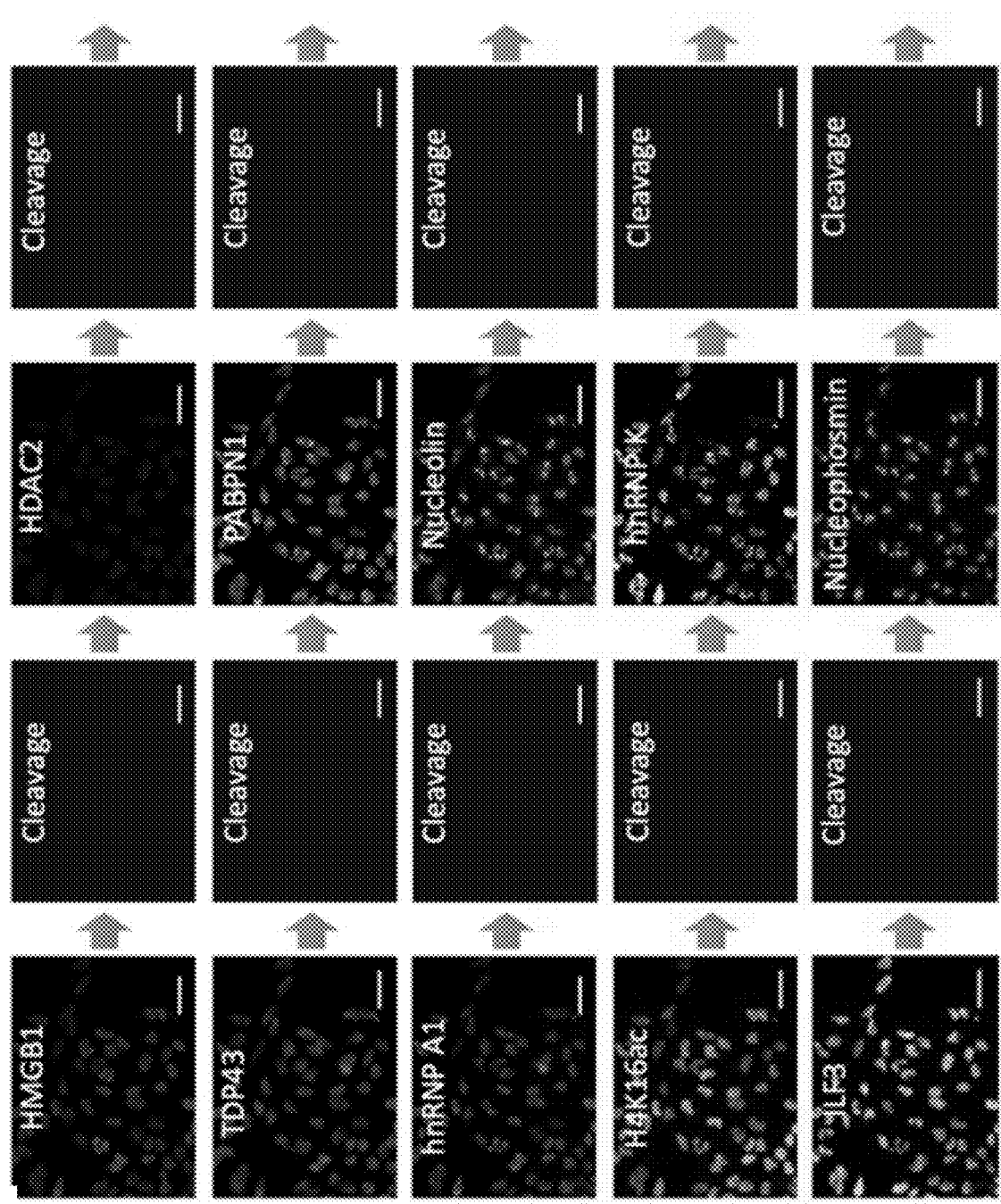
FIG. 5A-FIG. 5B. (A) 10 proteins are sequentially stained in the same set of HeLa cells with tyramide-$N_3$-Cy5. (B) 10 proteins are individually stained in different HeLa cells with conventional TSA. Scale bars, 50 μm.
Figure 5B:
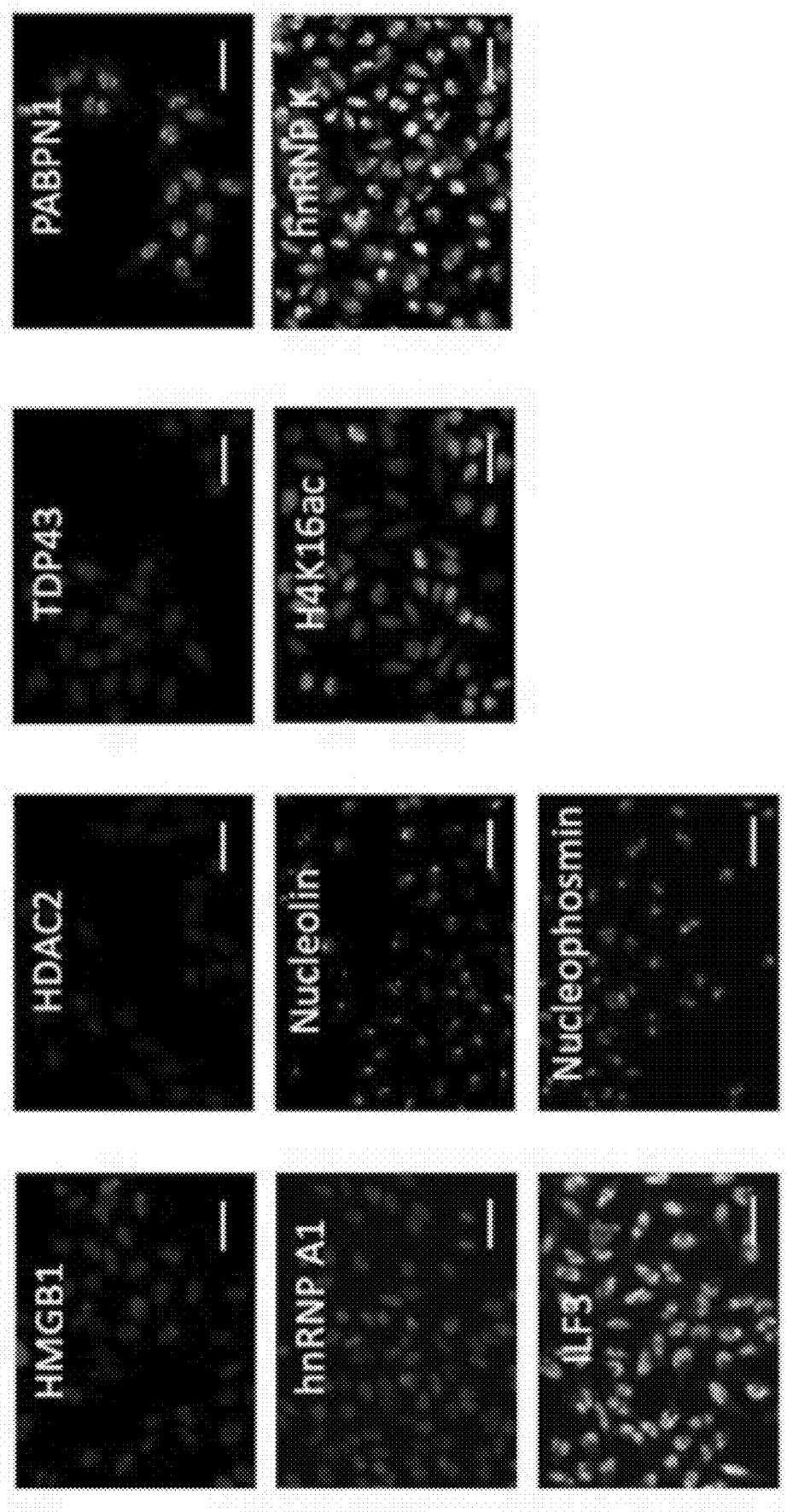
Figure 6B:
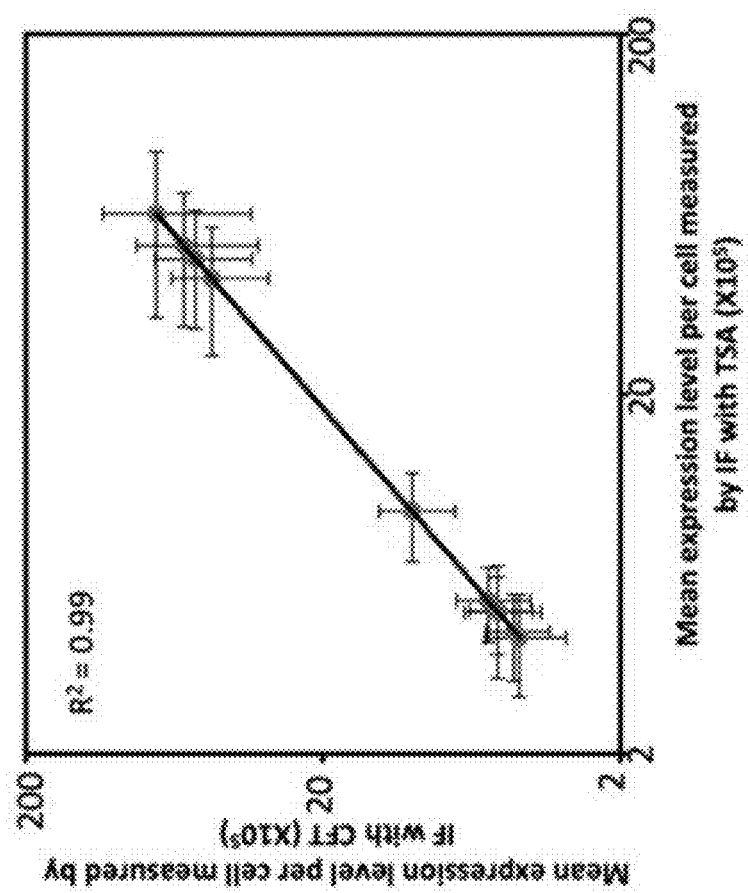
FIG. 6A-FIG. 6B. (A) Mean expression level per cell (n=100 cells) of the 10 proteins quantified by tyramide-$N_3$-Cy5 and conventional TSA. (B) Comparison of the results obtained by tyramide-$N_3$-Cy5 and TSA yields $R^2$=0.99 with a slope of 1.09.
Figure 6A:
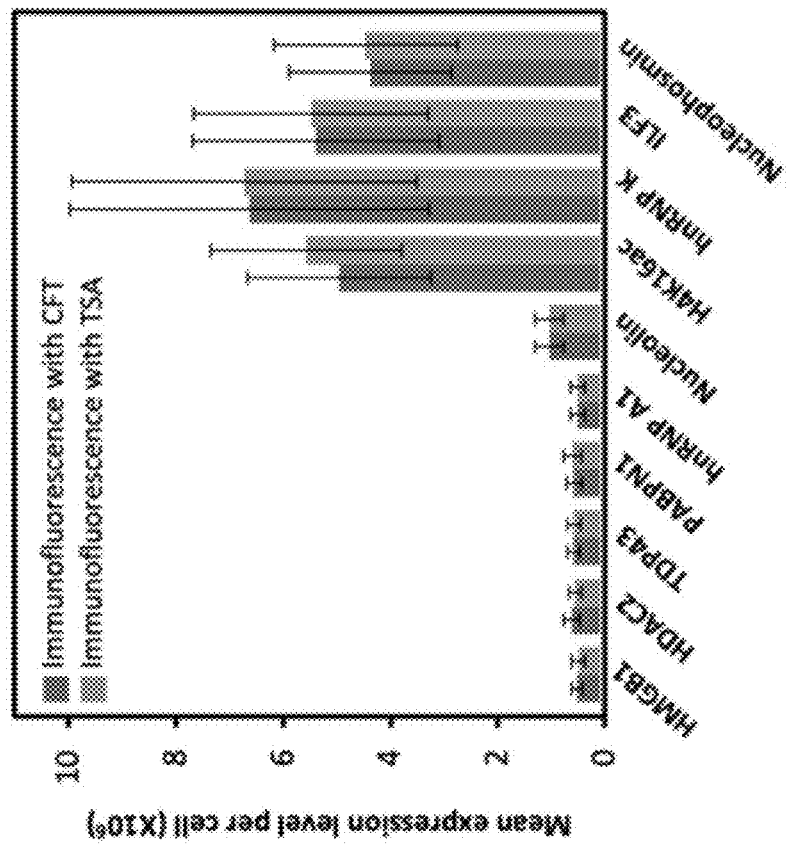

To explore whether the high-performance CFT can be applied for multiplexed protein imaging, we stained the 10 different proteins through reiterative immunofluorescence cycles in the same set of HeLa cells (FIG. 5A). As controls, we also stained each of those 10 target proteins using the conventional tyramide signal amplification (TSA) approach (FIG. 5B). The protein distribution patterns generated by the two approaches, together with the ones obtained with antibodies from varied clones [30,31], closely resemble each other. Additionally, the mean protein expression levels per cell obtained using our and TSA methods are also consistent (FIG. 6A). Comparison of the results measured by the two approaches generates an $R^2=0.99$ with a slope of 1.09 (FIG. 6B). These results suggest that our method enables the accurate and multiplexed protein analysis in single cells in situ.

2.6. Single-Cell Protein Expression Heterogeneity and Correlation

Figure 7A:
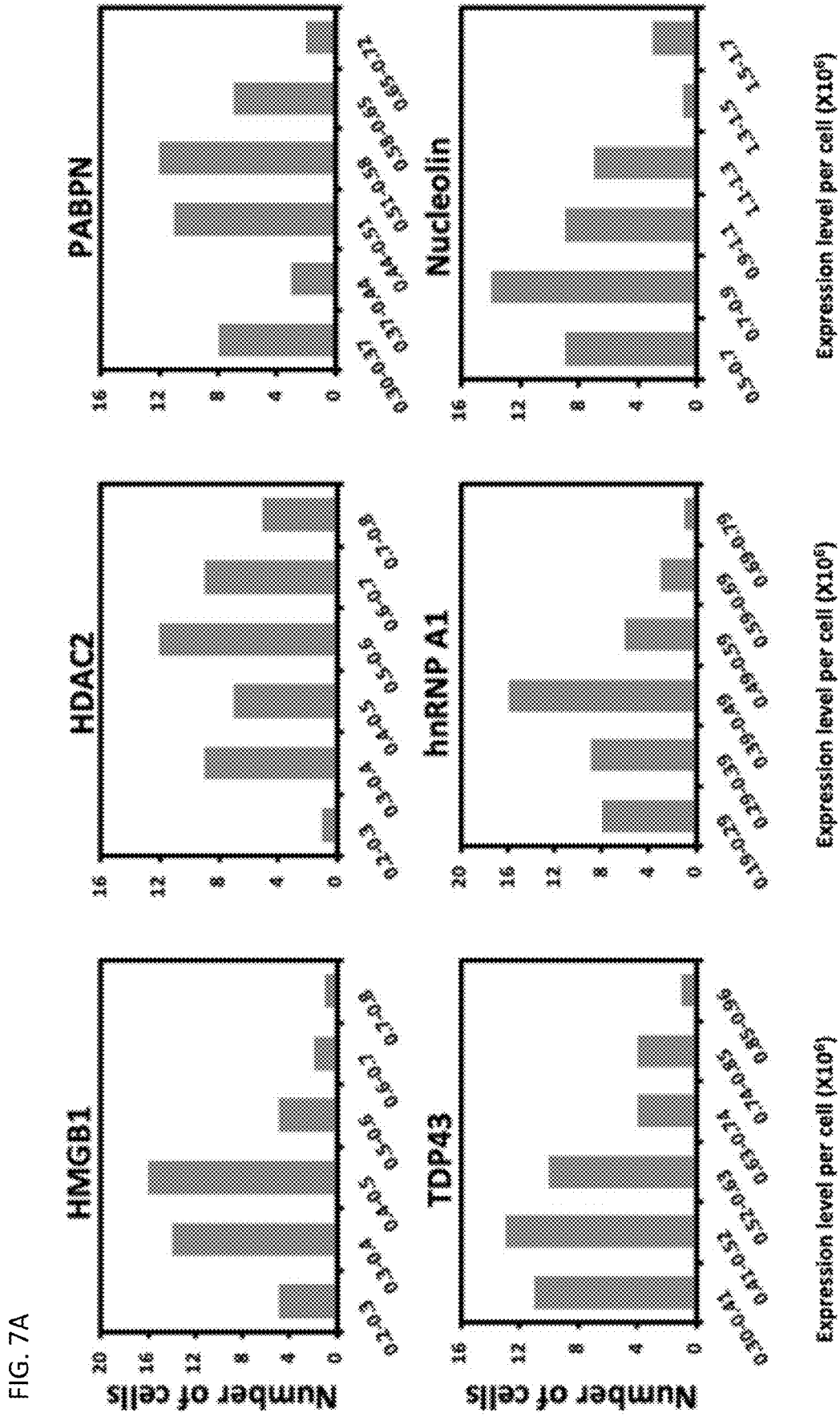
FIG. 7A-FIG. 7B. (A) Histograms of the expression level per cell for the 10 proteins stained in HeLa cells. (B) Pair-wise correlation of the expression levels of the 10 proteins and the hierarchical clustering tree. In the upper triangle, the expression correlation coefficients of every protein pair are shown. In the lower triangle, the color corresponds to the correlation coefficients of each protein pair. The diagonal displays the names of the proteins. With a threshold on the cluster tree (dashed line), a group of proteins with high expression correlation are identified and indicated by the red lines on the clustering tree and the black box in the matrix.

As reported previously, a group of genetically identical cells can have varied gene expression patterns at the single cell level [32-38]. To study such protein expression heterogeneity in individual HeLa cells, we quantified the distribution of the protein abundances in single cells (FIG. 7A). The expression levels of all the 10 analyzed proteins are distributed widely, which leads to the relatively large expression standard deviations in FIG. 6. And the square of those expression standard deviations is significantly higher than the average expression levels for each measured protein. These results suggest that the protein expression in individual HeLa cells is highly heterogeneous, which may be attributed to the synthesis of those proteins in bursts [39].

Figure 7B:
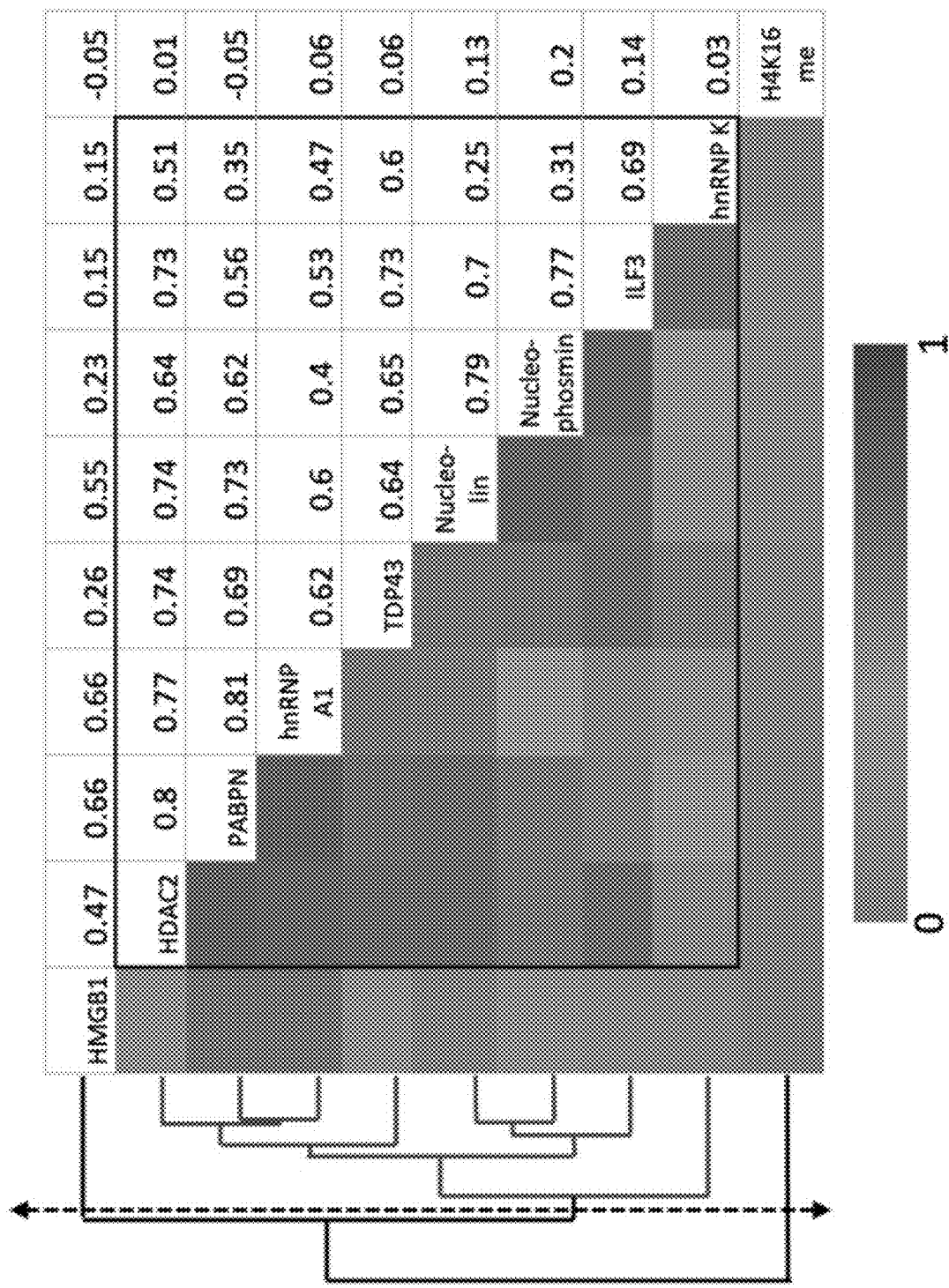

To explore which proteins are coregulated in a regulatory pathway, one can perform protein expression covariation analysis. Such studies carried out in populations of cells usually require external stimuli to induce different protein expression levels in varied cell groups. With the gene expression heterogeneity naturally generated in individual cells, single-cell protein expression covariation analysis can advance our understanding of regulatory pathways and predict the potential function of unannotated proteins [40]. To perform such studies, we calculated the pairwise expression correlation coefficient of the 10 analyzed proteins. Some protein pairs exhibit high expression correlation with the correlation efficient of ~0.8, including HDAC2 and PABPN together with PABPN and hnRNP A1. To elucidate the regulatory network among the 10 analyzed proteins, a hierarchical clustering method [41] was used and identified a group of 8 proteins with substantial expression correlation (FIG. 7B). As reported in the literature [42-49], those 8 proteins are indeed involved in the transcription processing and regulation pathways.

2.7. Multiplexed In Situ Protein Profiling in FFPE Tissues

Figure 8A:
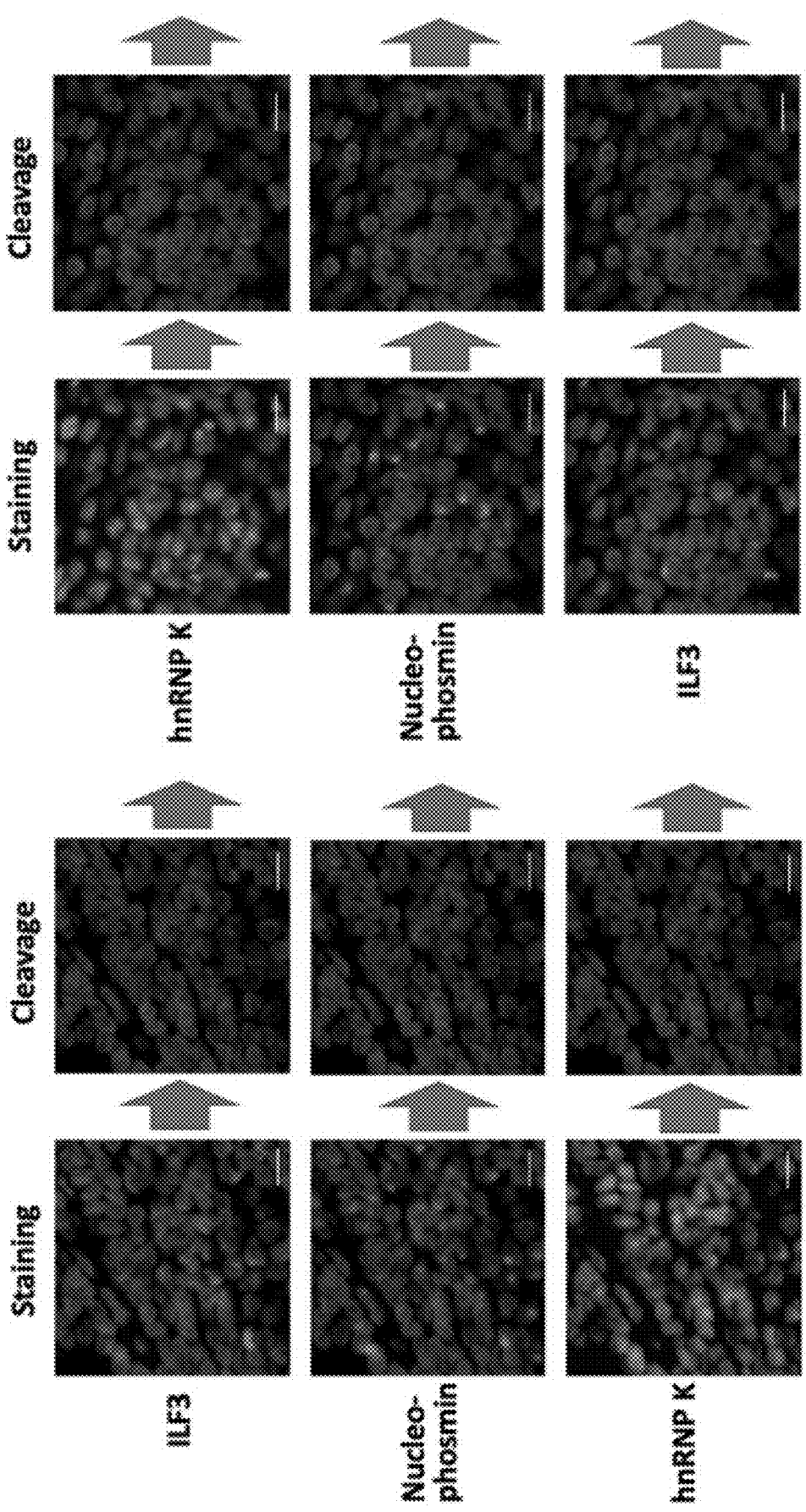
Figure 8C:
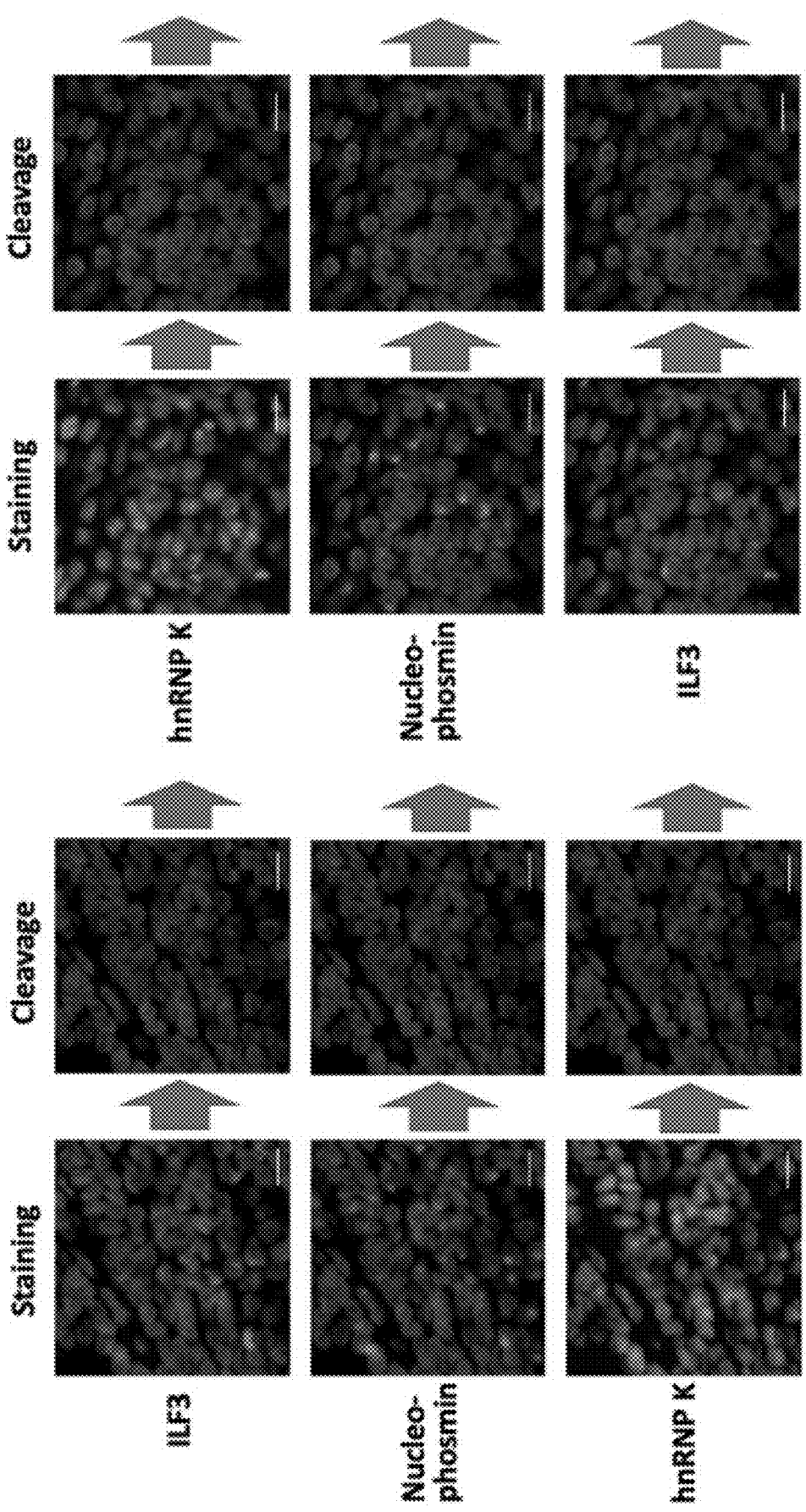
Figure 8D:
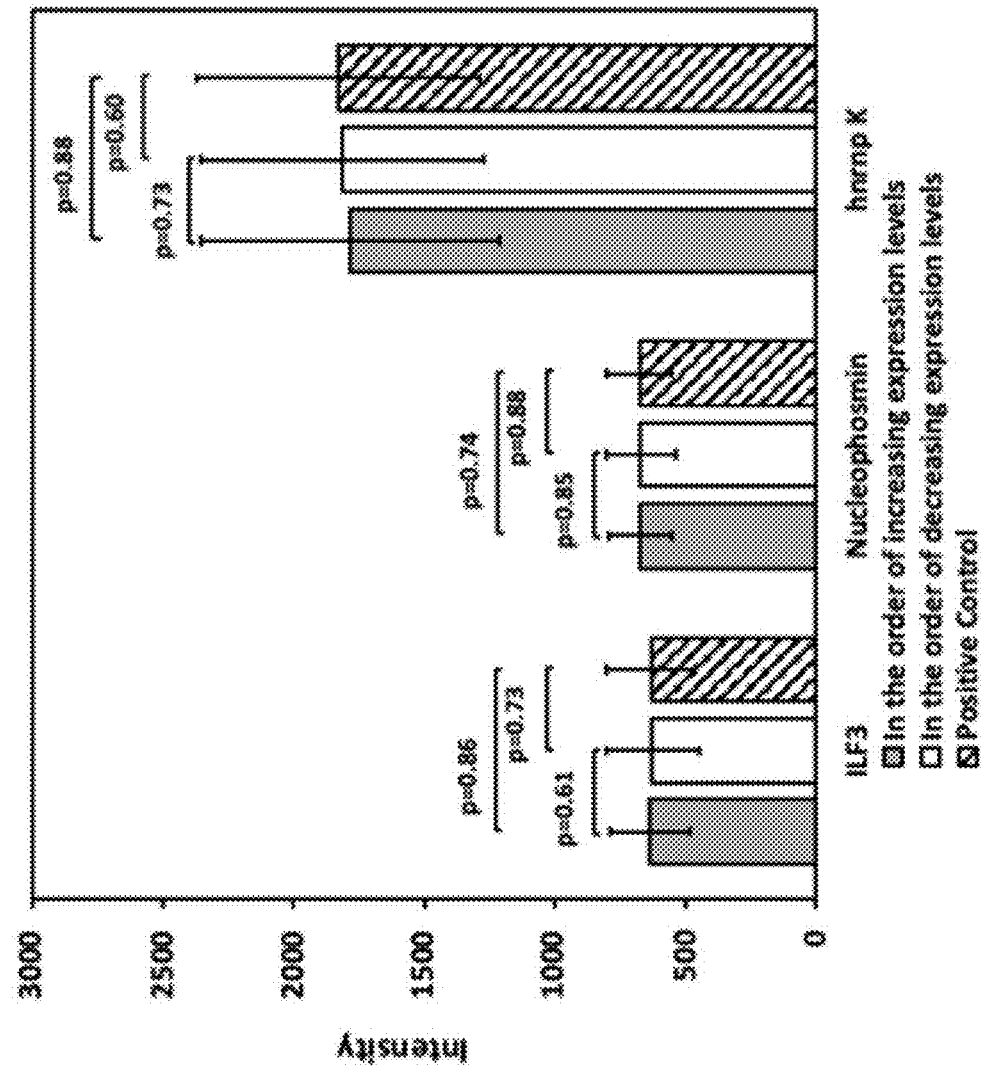
Figure 8B:
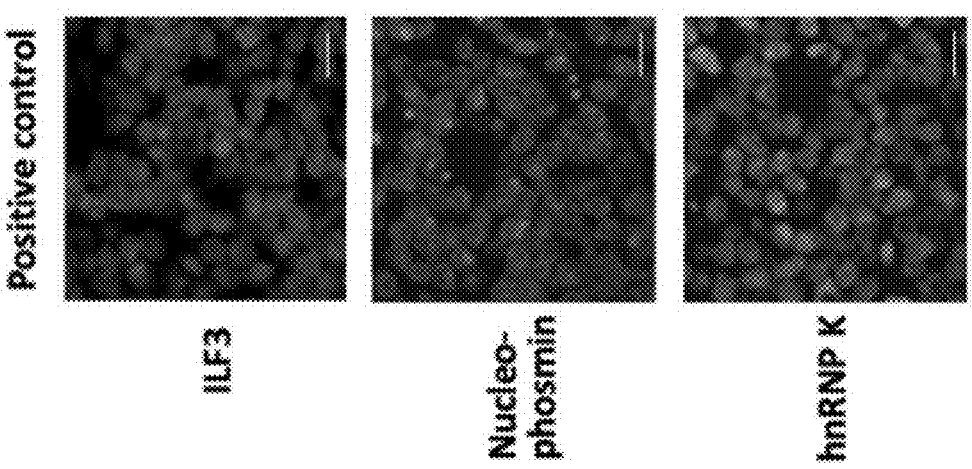

To demonstrate the feasibility of applying the high performance CFT for multiplexed protein analysis in FFPE tissues, we stained protein ILF3, Nucleophosmin, and hnRNP K through reiterative immunofluorescence cycles on a human FFPE tonsil tissue (FIG. 8A). We also stained these three proteins by the conventional TSA method (FIG. 8B). The staining patterns and signal intensities obtained by the two approaches are consistent with each other (FIG. 8D). These results indicate that multiplexed in situ protein profiling can be achieved in FFPE tissues using the high-performance CFT.

The existing reiterative protein staining approaches [7-12] require the proteins to be profiled in the order of increasing abundances, so that the leftover signals produced in the previous cycles may not interfere with the protein quantification in the following cycles. However, sometimes the amount of the precious clinical and biological samples is limited, and thus it can be impossible to have the knowledge of the relative protein expression levels in advance. Additionally, the order of the protein abundances in the varied cell types and states in the same specimen can be different. As a result, it might not be feasible to have an ideal protein analysis sequence that works for all the distinct cell types in the same specimen. Due to its high signal removal efficiency, our CFT approach may partially address those issues by eliminating the requirement of knowing the relative protein abundances in advance. To assess whether proteins can be profiled in the order of decreasing expression levels, we stained protein hnRNP K, Nucleophosmin and ILF3 sequentially on a human FFPE tonsil tissue (FIG. 8C). The generated staining patterns and signal intensities of all the three proteins closely resemble the ones obtained by the conventional TSA approach (FIG. 8D). These results suggest that the high signal removal efficiency of our approach enables it to partially eliminate the requirement of the prior knowledge of protein abundances and potentially allow accurate protein quantification regardless of the protein profiling order.

3. Discussion

In summary, we have design and synthesized the high performance CFT, and demonstrated it can be applied for multiplexed in situ protein profiling in culture cells and FFPE tissues. Compared the existing multiplexed protein imaging technologies, our approach has the following advantages. First, with the signal amplification by HRP, our approach has dramatically improved detection sensitivity. As a result, it enables the precise quantification of low-expression proteins in highly autofluorescent specimen, and also significantly enhance the sample throughput by reducing the imaging time. Second, as the commercially available and well validated antibodies are directly used in our approach, the time-consuming and expensive antibody-tag conjugation process is avoided. Third, by eliminating the carbamate group in the chemical structure of the high-performance CFT, the potential side reactions during CFT storage and protein staining are minimized. Finally, with the enhanced signal removal efficiency under a mild condition, our approach could allow multiple proteins to be precisely quantified regardless of the protein analysis order.

The multiplexing capacity of our approach depends on the number of reiterative analysis cycles and the number of proteins profiled in each cycle. We have shown that the protein antigeneity is preserved after the PTA overnight incubation, and we also documented previously that the integrity of the epitopes is maintained following the TCEP treatment for 24 hours [8]. As each signal removal reaction only requires 30 minutes of the PTA and TCEP incubation, we envision that at least 20 to 30 reiterative cycles can be performed on the same sample. In each analysis cycle, after staining the different protein targets using CFT with varied fluorophores, the HRP can be deactivated [50] or the antibodies can be stripped [51] using the established methods. In this way, four or five different proteins can be quantified in each cycle. As a result, we anticipate that our approach has the potential to enable ~100 proteins to be profiled in the same specimen.

The high-performance CFT developed here can also be applied for in situ analysis of nucleic acids [52] and metabolics [53]. By integrating these applications with protein analysis, the combined DNA, RNA, protein and metabolic analysis can be achieved in single cells in their natural spatial contexts. This highly multiplexed in situ molecular profiling platform will bring new insights into systems biology, biomedical research and precision medicine.

REFERENCES

1. Steininger, R. J.; Rajaram, S.; Girard, L.; Minna, J. D.; Wu, L. F.; Altschuler, S. J. On comparing heterogeneity across biomarkers. *Cytom. Part A* 2015, 87, 558-567, doi:10.1002/cyto.a.22599.
2. Junker, J. P.; Van Oudenaarden, A. Every cell is special: Genome-wide studies add a new dimension to single-cell biology. *Cell* 2014, 157, 8-11, doi:10.1016/j.cell.2014.02.010.
3. LaBaer, J.; Ramachandran, N. Protein microarrays as tools for functional proteomics. *Curr. Opin. Chem. Biol.* 2005, 9, 14-19. doi: 10.1016/j.cbpa.2004.12.006.

4. Altelaar, a F. M.; Munoz, J.; Heck, A. J. R. Next-generation proteomics: towards an integrative view of proteome dynamics. *Nat. Rev. Genet.* 2012, 14, 35-48, doi:10.1038/nrg3356.
5. Guo, J.; Wang, S.; Dai, N.; Teo, Y. N.; Kool, E. T. Multispectral labeling of antibodies with polyfluorophores on a DNA backbone and application in cellular imaging. *Proc. Natl. Acad. Sci.* 2011, 108, 3493-3498, doi:10.1073/pnas.1017349108.
6. Angelo, M.; Bendall, S. C.; Finck, R.; Hale, M. B.; Hitzman, C.; Borowsky, A. D.; Levenson, R. M.; Lowe, J. B.; Liu, S. D.; Zhao, S.; et al. Multiplexed ion beam imaging of human breast tumors. Nat. Med. 2014, 20, 436-442, doi:10.1038/nm.3488.
7. Robertson, D.; Savage, K.; Reis-Filho, J. S.; Isacke, C. M. Multiple immunofluorescence labeling of formalin-fixed paraffin-embedded tissue. *BMC Mol. Biol.*2008, 9, 1-10, doi:10.1007/978-1-61779-055-3_4.
8. Mondal, M.; Liao, R.; Xiao, L.; Eno, T.; Guo, J. Highly Multiplexed Single-Cell In Situ Protein Analysis with Cleavable Fluorescent Antibodies. *Angew. Chemie Int. Ed.* 2017, 56, 2636-2639, doi:10.1002/anie.201611641.
9. Schweller, R. M.; Zimak, J.; Duose, D. Y.; Qutub, A. a; Hittelman, W. N.; Diehl, M. R. Multiplexed in situ immunofluorescence using dynamic DNA complexes. *Angew. Chem. Int. Ed. Engl.* 2012, 51, 9292-9296, doi:10.1002/anie.201204304.
10. Duose, D. Y.; Schweller, R. M.; Zimak, J.; Rogers, A. R.; Hittelman, W. N.; Diehl, M. R. Configuring robust DNA strand displacement reactions for in situ molecular analyses. *Nucleic Acids Res.* 2012, 40, 3289-3298, doi:10.1093/nar/gkr1209.
11. Zrazhevskiy, P.; Gao, X. Quantum dot imaging platform for single-cell molecular profiling. *Nat. Commun.*2013, 4, 1619, doi:10.1038/ncomms2635.
12. Lin, J. R.; Fallahi-Sichani, M.; Sorger, P. K. Highly multiplexed imaging of single cells using a high-throughput cyclic immunofluorescence method. *Nat. Commun.* 2015, 6, 1-7, doi:10.1038/ncomms9390.
13. Goltsev, Y.; Samusik, N.; Kennedy-Darling, J.; Bhate, S.; Hale, M.; Vazquez, G.; Black, S.; Nolan, G. P. Deep Profiling of Mouse Splenic Architecture with CODEX Multiplexed Imaging. Cell 2018, 174, 968-981.e15, doi:10.1016/j.cell.2018.07.010.
14. Giesen, C.; Wang, H. a O.; Schapiro, D.; Zivanovic, N.; Jacobs, A.; Hattendorf, B.; Schüffler, P. J.; Grolimund, D.; Buhmann, J. M.; Brandt, S.; et al. Highly multiplexed imaging of tumor tissues with subcellular resolution by mass cytometry. Nat. Methods 2014, 11, 417-422, doi: 10.1038/nmeth.2869.
15. Liao, R.; Pham, T.; Mastroeni, D.; Coleman, P. D.; Labaer, J.; Guo, J. Highly Sensitive and Multiplexed In-Situ Protein Profiling with Cleavable Fluorescent Streptavidin. *Cells* 2020, 9, 852, doi:10.3390/cells9040852.
16. Saka, S. K.; Wang, Y.; Kishi, J. Y.; Zhu, A.; Zeng, Y.; Xie, W.; Kirli, K.; Yapp, C.; Cicconet, M.; Beliveau, B. J.; et al. Immuno-SABER enables highly multiplexed and amplified protein imaging in tissues. *Nat. Biotechnol.* 2019, 37, 1080-1090, doi:10.1038/s41587-019-0207-y.
17. Liao, R.; Mondal, M.; Nazaroff, C. D.; Mastroeni, D.; Coleman, P. D.; Labaer, J.; Guo, J. Highly Sensitive and Multiplexed Protein Imaging With Cleavable Fluorescent Tyramide Reveals Human Neuronal Heterogeneity. *Front. Cell Dev. Biol.* 2021, 8, 1-15, doi:10.3389/fcell.2020.614624.
18. Mondal, M.; Liao, R.; Nazaroff, C. D.; Samuel, A. D.; Guo, J. Highly multiplexed single-cell in situ RNA and DNA analysis with bioorthogonal cleavable fluorescent oligonucleotides. *Chem. Sci.* 2018, 9, 2909-2917, doi: 10.1039/C7SC05089E.
19. Jun, Y. W.; Kim, H. R.; Reo, Y. J.; Dai, M.; Ahn, K. H. Addressing the autofluorescence issue in deep tissue imaging by two-photon microscopy: The significance of far-red emitting dyes. *Chem. Sci.* 2017, 8, 7696-7704, doi:10.1039/c7sc03362a.
20. Lin, Y. H.; Yao, M. C.; Wu, H. Y.; Dong, J.; Ni, H. Y.; Kou, X. L.; Chang, L.; Luo, C. X.; Zhu, D. Y. HDAC2 (Histone deacetylase 2): A critical factor in environmental enrichment-mediated stroke recovery. *J. Neurochem.* 2020, 155, 679-696. doi:10.1111/jnc.15043.
21. Zhao, L.; Ke, H.; Xu, H.; Wang, G. D.; Zhang, H.; Zou, L.; Xiang, S.; Li, M.; Peng, L.; Zhou, M.; et al. TDP-43 facilitates milk lipid secretion by post-transcriptional regulation of Btn1a1 and Xdh. *Nat. Commun.* 2020, 11, 341. doi:10.1038/s41467-019-14183-1.
22. Harish, P.; Forrest, L.; Herath, S.; Dickson, G.; Malerba, A.; Popplewell, L. Inhibition of Myostatin Reduces Collagen Deposition in a Mouse Model of Oculopharyngeal Muscular Dystrophy (OPMD) With Established Disease. *Front. Physiol.* 2020, 11, 184. doi:10.3389/fphys.2020.00184.
23. Jia, Q.; Nie, H.; Yu, P.; Xie, B.; Wang, C.; Yang, F.; Wei, G.; Ni, T. HNRNPA1-mediated 3′ UTR length changes of HN1 contributes to cancer- and senescence-associated phenotypes. *Aging* (Albany. NY). 2019, 11, 4407-4437, doi:10.18632/aging.102060.
24. Dubois, M. L.; Meller, A.; Samandi, S.; Brunelle, M.; Frion, J.; Brunet, M. A.; Toupin, A.; Beaudoin, M. C.; Jacques, J. F.; Lévesque, D.; et al. UBB pseudogene 4 encodes functional ubiquitin variants. *Nat. Commun.* 2020, 11, 1306. doi:10.1038/s41467-020-15090-6.
25. Li, L.; Ghorbani, M.; Weisz-Hubshman, M.; Rousseau, J.; Thiffault, I.; Schnur, R. E.; Breen, C.; Oegema, R.; Weiss, M. M. M.; Waisfisz, Q.; et al. Lysine acetyltransferase 8 is involved in cerebral development and syndromic intellectual disability. *J. Clin. Invest.* 2020, 130, 1431-1445, doi:10.1172/JCI131145.
26. Pellegrini, L.; Hauser, D. N.; Li, Y.; Mamais, A.; Beilina, A.; Kumaran, R.; Wetzel, A.; Nixon-Abell, J.; Heaton, G.; Rudenko, I.; et al. Proteomic analysis reveals co-ordinated alterations in protein synthesis and degradation pathways in LRRK2 knockout mice. *Hum. Mol. Genet.* 2018, 27, 3257-3271, doi:10.1093/hmg/ddy232.
27. Watson, S. F.; Bellora, N.; Maclas, S. ILF3 contributes to the establishment of the antiviral type i interferon program. *Nucleic Acids Res.* 2020, 48, 116-129, doi: 10.1093/nar/gkz1060.
28. Chen, Q.; Xi, X.; Zeng, Y.; He, Z.; Zhao, J.; Li, Y. Acteoside inhibits autophagic apoptosis of retinal ganglion cells to rescue glaucoma-induced optic atrophy. *J. Cell. Biochem.* 2019, 120, 13133-13140, doi:10.1002/jcb.28586.
29. Maugeri, N.; Campana, L.; Gavina, M.; Covino, C.; De Metrio, M.; Panciroli, C.; Maiuri, L.; Maseri, A.; D'Angelo, A.; Bianchi, M. E.; et al. Activated platelets present high mobility group box 1 to neutrophils, inducing autophagy and promoting the extrusion of neutrophil extracellular traps. *J. Thromb. Haemost.* 2014, 12, 2074-2088, doi:10.1111/jth.12710.
30. Uhlén, M.; Fagerberg, L.; Hallstrom, B. M.; Lindskog, C.; Oksvold, P.; Mardinoglu, A.; Sivertsson, Å.; Kampf, C.; Sjöstedt, E.; Asplund, A.; et al. Tissue-based map of the human proteome. *Science* 2015, 347, 1260419, doi:10.1126/science.1260419.
31. Thul, P. J.; Akesson, L.; Wiking, M.; Mandessian, D.; Geladaki, A.; Ait Blal, H.; Alm, T.; Asplund, A.; Björk, L.; Breckels, L. M.; et al. A subcellular map of the human proteome. *Science.* 2017, 356, doi:10.1126/science.aal3321.
32. Becskei, A.; Kaufmann, B. B.; van Oudenaarden, A. Contributions of low molecule number and chromosomal positioning to stochastic gene expression. *Nat. Genet.* 2005, 37, 937-944, doi:10.1038/ng1616.
33. Blake, W. J.; KAErn, M.; Cantor, C. R.; Collins, J. J. Noise in eukaryotic gene expression. *Nature* 2003, 422, 633-637, doi:10.1038/nature01546.
34. Elowitz, M. B.; Levine, A. J.; Siggia, E. D.; Swain, P. S. Stochastic gene expression in a single cell. *Science* 2002, 297, 1183-1186, doi:10.1126/science.1070919.
35. Golding, I.; Paulsson, J.; Zawilski, S. M.; Cox, E. C. Real-time kinetics of gene activity in individual bacteria. *Cell* 2005, 123, 1025-1036, doi:10.1016/j.cell.2005.09.031.
36. Ozbudak, E. M.; Thattai, M.; Kurtser, I.; Grossman, A. D.; van Oudenaarden, A. Regulation of noise in the expression of a single gene. *Nat. Genet.* 2002, 31, 69-73, doi:10.1038/ng869.
37. Raser, J. M.; O'Shea, E. K. Control of stochasticity in eukaryotic gene expression. *Science* 2004, 304, 1811-1814, doi:10.1126/science.1098641.
38. Rosenfeld, N.; Young, J. W.; Alon, U.; Swain, P. S.; Elowitz, M. B. Gene Regulation at the Single-Cell Level. *Science* 2005, 307, 1962-1965.
39. Raj, A.; Peskin, C. S.; Tranchina, D.; Vargas, D. Y.; Tyagi, S. Stochastic mRNA synthesis in mammalian cells. *PLoS Biol.* 2006, 4, 1707-1719, doi:10.1371/journal.pbio.0040309.
40. Munsky, B.; Neuert, G.; van Oudenaarden, a. Using Gene Expression Noise to Understand Gene Regulation. *Science.* 2012, 336, 183-187, doi:10.1126/science.1216379.
41. Eisen, Michael B., Spellman, Paul T., Brown, Patrick O., Botstein, D. Cluster analysis and display of genome-wide expression patterns. *Proc. Natl. Acad. Sci. USA* 1998, 95, 14863-14868.
42. Jahan, S.; Sun, J.-M.; He, S.; Davie, J. R. Transcription-dependent association of HDAC2 with active chromatin. *J. Cell. Physiol.* 2018, 233, 1650-1657, doi:10.1002/jcp.26078.
43. Lalmansingh, A. S.; Urekar, C. J.; Reddi, P. P. TDP-43 is a transcriptional repressor: the testis-specific mouse acrv1 gene is a TDP-43 target in vivo. *J. Biol. Chem.* 2011, 286, 10970-10982, doi:10.1074/jbc.M110.166587.
44. Jean-Philippe, J.; Paz, S.; Caputi, M. hnRNP A1: the Swiss army knife of gene expression. *Int. J. Mol. Sci.* 2013, 14, 18999-19024, doi:10.3390/ijms140918999.
45. Abdelmohsen, K.; Gorospe, M. RNA-binding protein nucleolin in disease. *RNA Biol.* 2012, 9, 799-808, doi:10.4161/rna.19718.
46. Box, J. K.; Paquet, N.; Adams, M. N.; Boucher, D.; Bolderson, E.; O'Byrne, K. J.; Richard, D. J. Nucleophosmin: from structure and function to disease development. *BMC Mol. Biol.* 2016, 17, 19, doi:10.1186/s12867-016-0073-9.
47. Banerjee, A.; Apponi, L. H.; Pavlath, G. K.; Corbett, A. H. PABPN1: molecular function and muscle disease. *FEBS J* 2013, 280, 4230-4250, doi:10.1111/febs.12294.
48. Castella, S.; Bernard, R.; Corno, M.; Fradin, A.; Larcher, J.-C. Ilf3 and NF90 functions in RNA biology. *Wiley Interdiscip. Rev. RNA* 2015, 6, 243-256, doi:10.1002/wrna.1270.
49. Lu, J.; Gao, F.-H. Role and molecular mechanism of heterogeneous nuclear ribonucleoprotein K in tumor development and progression. *Biomed. reports* 2016, 4, 657-663, doi:10.3892/br.2016.642.
50. Liu, G.; Amin, S.; Okuhama, N. N.; Liao, G.; Mingle, L. A. A quantitative evaluation of peroxidase inhibitors for tyramide signal amplification mediated cytochemistry and histochemistry. *Histochem. Cell Biol.* 2006, 126, 283-291, doi:10.1007/s00418-006-0161-x.
51. Stack, E. C.; Wang, C.; Roman, K. A.; Hoyt, C. C. Multiplexed immunohistochemistry, imaging, and quantitation: A review, with an assessment of Tyramide signal amplification, multispectral imaging and multiplex analysis. *Methods* 2014, 70, 46-58, doi:10.1016/j.ymeth.2014.08.016.
52. van de Corput, M. P.; Dirks, R. W.; van Gijlswijk, R. P.; van de Rijke, F. M.; Raap, A. K. Fluorescence in situ hybridization using horseradish peroxidase-labeled oligodeoxynucleotides and tyramide signal amplification for sensitive DNA and mRNA detection. *Histochem. Cell Biol.* 1998, 110, 431-437.
53. Xue, M.; Wei, W.; Su, Y.; Kim, J.; Shin, Y. S.; Mai, W. X.; Nathanson, D. a.; Heath, J. R. Chemical methods for the simultaneous quantitation of metabolites and proteins from single cells. *J. Am. Chem. Soc.* 2015, 137, 4066-4069, doi:10.1021/jacs.5b00944.

The present invention has been described in terms of one or more embodiments, and it should be appreciated that many equivalents, alternatives, variations, and modifications, aside from those expressly stated, are possible and within the scope of the invention.

We claim:

1. A compound of Formula (I):

wherein R is a detectable marker selected from the group consisting of fluorophores, luminescent agents, fluorescent proteins, and radioisotopes.

2. The compound of claim 1 wherein the detectable marker is selected from the group consisting of Cy5, TAMRA, and ATTO 647N and ATTO 700 fluorophores, quantum dots, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red, and Cy2, Cy3.5, Cy5.5, Cy7, sulfonated Cy2, Cy3.5, Cy 5, Cy5.5, and Cy7.

3. The compound of claim 1, wherein the detectable marker is a fluorophore.

4. The compound of claim 3, wherein the fluorophore is selected from the group consisting of Cy5, TAMRA, ATTO 647N, and ATTO 700.

5. The compound of claim 1, wherein the compound is Formula (II):

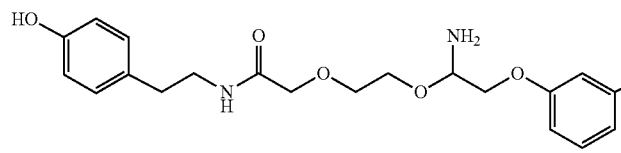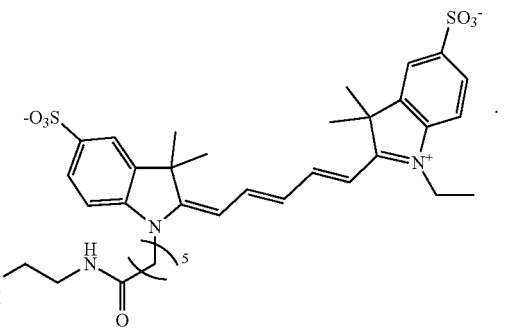

Formula II

6. A method of multiplex in situ analysis of biomolecules in a tissue sample, the method comprising:
   (a) contacting a tissue sample with a first plurality of horseradish peroxidase (HRP)-conjugated targeting agents that specifically bind to or hybridize to a first target biomolecule in the tissue sample;
   (b) contacting the tissue sample with the compound of claim 1;
   (c) imaging the tissue sample thereby detecting the detectable marker;
   (d) contacting the tissue sample with a composition comprising 1,3,5-Triaza-7-phosphaadamantane (PTA) and tris(2-carboxyethyl)phosphine (TCEP);
   (e) repeating steps (a)-(d); wherein a second plurality of HRP-conjugated targeting agents is used to bind to or hybridize to a second target biomolecule, wherein the first and the second target biomolecules are different.

7. The method of claim 6, wherein the first plurality of targeting agents comprises HRP-conjugated synthetic DNA oligonucleotide probes.

8. The method of claim 6, wherein the first plurality of targeting agents comprises HRP-conjugated polyclonal antibodies, HRP-conjugated monoclonal antibodies, or HRP-conjugated antigen-binding fragments thereof.

9. The method of claim 6, wherein the first target biomolecules are less abundant in the sample tissue than the second target biomolecules.

10. The method of claim 6, wherein the tissue sample is a biopsy sample.

11. The method of claim 6, wherein the tissue sample is a formalin-fixed and paraffin-embedded tissue sample.

12. The method of claim 6, wherein the detectable marker is a fluorophore.

13. The method of claim 6, wherein the compound of contacting step (b) is Formula II:

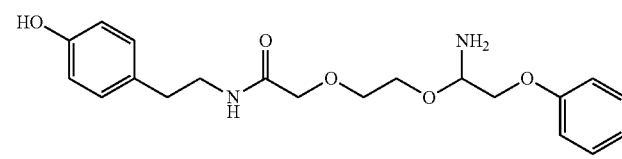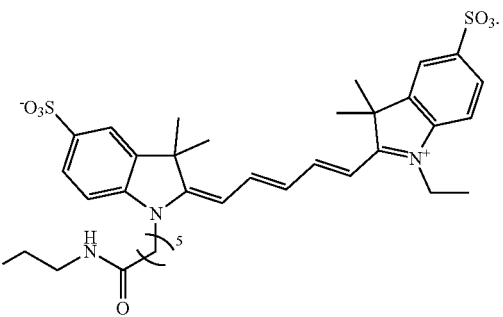

14. The method of claim 6, wherein step (d) comprises incubating the contacted sample at about 40° C. for about 30 minutes.

15. A kit comprising:
(a) a composition comprising the compound of Formula I or Formula II:
wherein Formula I is:

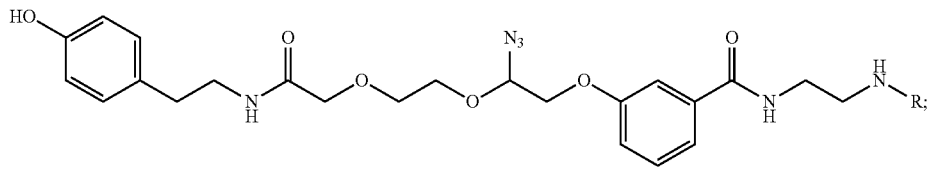

wherein R is a detectable marker selected from the group consisting of fluorophores, luminescent agents, fluorescent proteins, and radioisotopes;
wherein Formula II is:

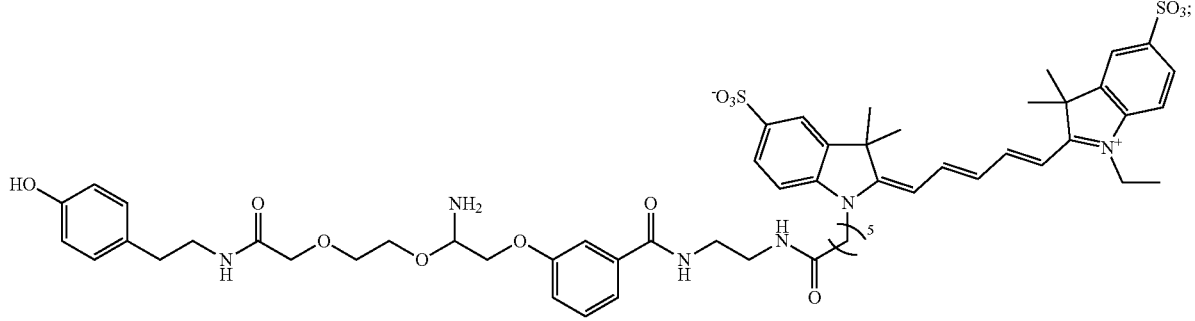

(b) a composition comprising 1,3,5-Triaza-7-phosphaadamantane (PTA); and
(c) a composition comprising tris(2-carboxyethyl)phosphine (TCEP).

16. The kit of claim 15, comprising the compound of Formula II.

17. The kit of claim 15, further comprising:
(d) horseradish peroxidase (HRP)-conjugated targeting agents.

* * * * *

UNITED STATES PATENT AND TRADEMARK OFFICE
CERTIFICATE OF CORRECTION

Page 1 of 2

PATENT NO. : 12,385,924 B2
APPLICATION NO. : 17/694353
DATED : August 12, 2025
INVENTOR(S) : Jia Guo et al.

It is certified that error appears in the above-identified patent and that said Letters Patent is hereby corrected as shown below:

In the Specification

Column 3, " 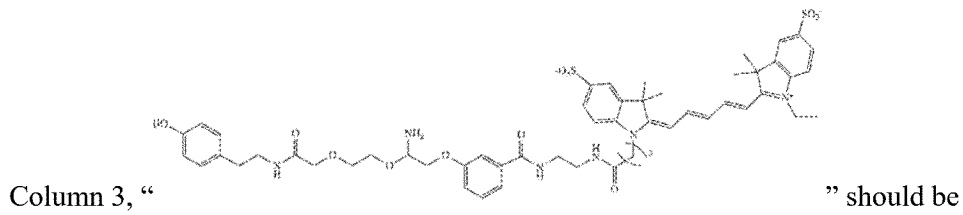 " should be

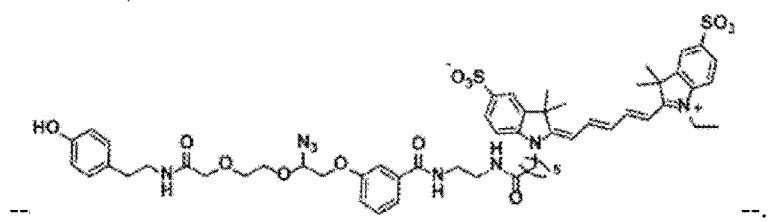 --.

Column 6, " 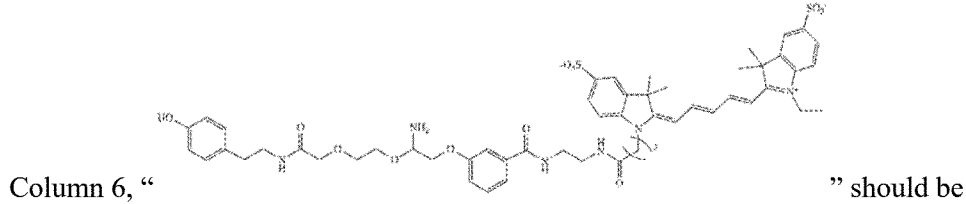 " should be

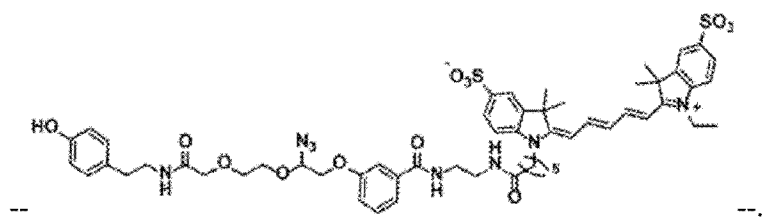 --.

Signed and Sealed this
Ninth Day of December, 2025

John A. Squires
*Director of the United States Patent and Trademark Office*

CERTIFICATE OF CORRECTION (continued)
U.S. Pat. No. 12,385,924 B2

In the Claims

Column 27 and 28, Claim 5, " 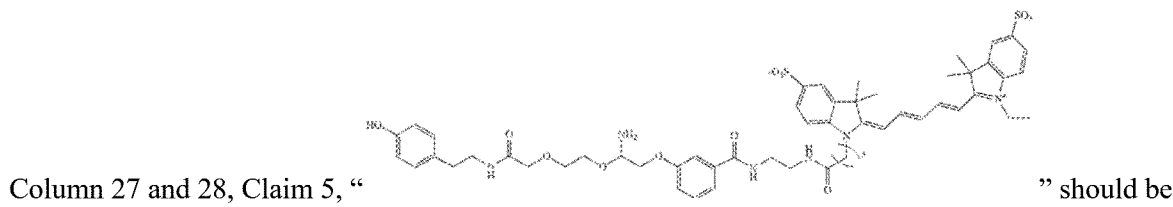 " should be

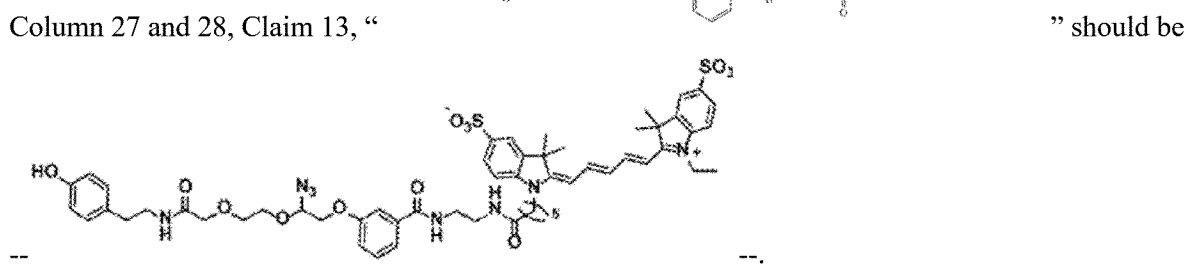

-- --.

Column 27 and 28, Claim 13, " 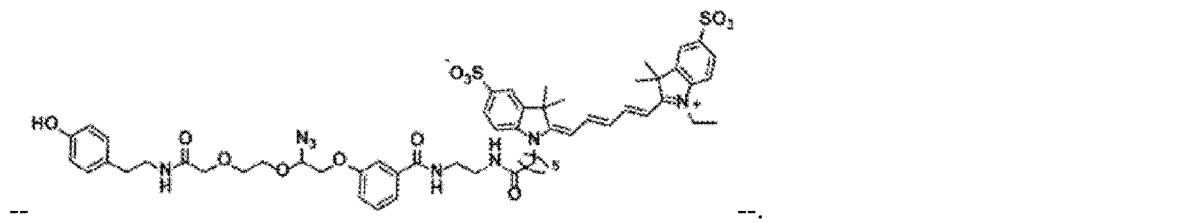 " should be

-- --.

Column 29 and 30, Claim 15, " " should be

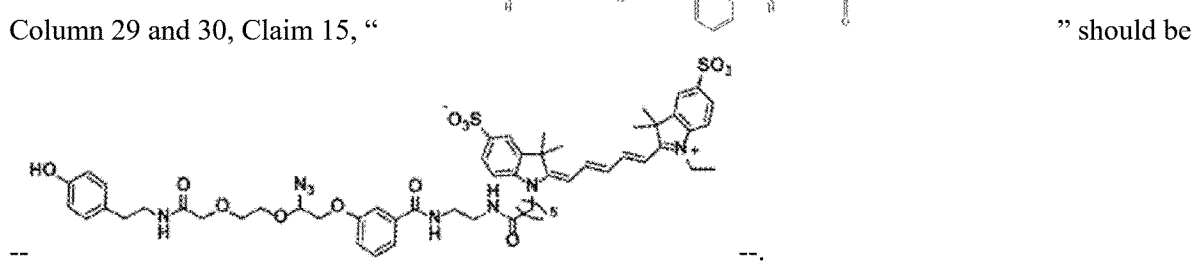

-- --.